US007235534B2

(12) United States Patent
Tanguay et al.

(10) Patent No.: US 7,235,534 B2
(45) Date of Patent: Jun. 26, 2007

(54) ANTISENSE STRATEGY TO MODULATE ESTROGEN RECEPTOR RESPONSE (ER α AND/OR ER β)

(75) Inventors: Jean-François Tanguay, Montréal (CA); Martin Sirois, Anjou (CA)

(73) Assignee: Institut de Cardiologie de Montreal, Montreal, Quebec (CA)

( * ) Notice: Subject to any disclaimer, the term of this patent is extended or adjusted under 35 U.S.C. 154(b) by 90 days.

(21) Appl. No.: 10/327,776

(22) Filed: Dec. 23, 2002

(65) Prior Publication Data
US 2003/0144240 A1 Jul. 31, 2003

(30) Foreign Application Priority Data
Dec. 21, 2001 (CA) .................................. 2365811

(51) Int. Cl.
*C07H 21/04* (2006.01)
*C07H 21/02* (2006.01)
*A61K 48/00* (2006.01)
(52) U.S. Cl. ...................... 514/44; 536/23.1; 536/24.5
(58) Field of Classification Search .................. 514/44; 536/23.1, 24.3, 24.31, 24.5
See application file for complete search history.

(56) References Cited

U.S. PATENT DOCUMENTS 5,958,710 A 9/1999 Kuiper et al. ............... 435/7.21

FOREIGN PATENT DOCUMENTS

| WO | WO 99/54459 | * | 10/1999 | .................. 514/44 |
| WO | WO 01/69262 A1 | * | 9/2001 | .................. 514/44 |
| WO | WO 03/050133 A1 | * | 6/2003 | .................. 514/44 |

OTHER PUBLICATIONS

Branch, A good antisense molecule is hard to find, TIBS, Feb. 1998, pp. 45-50.*
Green et al., Antisense Oligonucleotides: An Evolving Technology for the Modulation of Gene Expression in Human Disease, J Am Coll Surg, Jul. 2000, vol. 191, No. 1, pp. 93-105.*
Jen et al., Suppression of Gene Expression by Targeted Disruption of Messenger RNA: Available Options and Current Strategies, Stem Cells, 2000, 18:307-319.*
Crooke, ST et al., Pharmacokinetic properties of several novel oligonucleotide analogs in mice. vol. 277, Issue 2, pp. 923-937, May 1, 1996, Copyright 1996 by American Society for Pharmacology and Experimental Therapeutics.
Johnston, Stephen A. et al., Functional Domains of the Yeast Regulatory Protein GAL4, Proceedings of the National Academy of Sciences of the United States of America, vol. 83, Issue 17 (Sep. 1, 1986), 6553-6557.
Manoharan, M et al., Introduction of a Lipophilic Thioether Tether in the Minor Groove of Nucleic Acids for Antinsense Applications, Bioorganic & Medicinal Chemistry Letters, vol. 3, No. 12, pp. 2765-2770, 1993.

Manoharan, M et al., Lipidic Nucleic Acids, Tetrahedron Letter, vol. 36, No. 21, pp. 3651-3654, 1995.
Manoharan, M et al., Cholic Acid-Oligonucleotide Conjugates for Antisense Applications, Bioorganic & MedicinalChemistry Letter, vol. 4, No. 8, pp. 1053-1060, 1994.
Mishra, R et al., Improved leishmanicidal effect of phosphorotioate antisense oligonucleotides by LDL-mediated delivery, Biochimica et Biophysica Acta 1264 (1995) 229-237, 1995.
Nielsen, P et al., Sequence-Selective Recognition of DNA by Strand Displacement with a Thymine-Substituted Polyamide, Science; Dec. 6, 1991;254,5037; Research Library Core p. 1497.
Oberhauser, B and Wagner, E., Effective incorporation of 2'-O'methyl-oligoribonucleotides into liposomes and enhanced cell association through modification with thiocholesterol, Institute of Molecular Pathology, Vienna, Austria, abstract only.
Saison-Behmoaras, T et al., Short modified antisense oligonucleotides directed against Haras point mutation induce selective cleavage of the MRNA and inhbit T24 cells prliferation, The EMBO Journal, vol. 10, pp. 1111-1118, 1991. Copyright European Molecular Biology Organization, abstract only.
Shea, R et al., Synthesis, hybridization properties and antiviral activity of lipid-oligodeoxynucleotide conjugates, NucleicAcids Research, vol. 18, Issue 13, pp. 3888-3783, Copyright 1990 by Oxford University Press, abstract only.
Crooke, S et al., Antisense Research and Applications, ISBN: 084934705x, Publication Date: May 27, 1993, abstract only.
Manorharan, M et al., Chemical modifications to improve uptake and bioavailability of antisense oligonucleotides, Ann NY Acad Aci, 1992 660, pp. 306-309.
Cignarella A., Paoletti R., Puglisi L.; Direct Effects of Estrogen on the Vessel Wall; Med. Res. Rev.; 2001;21:171-84.
Song, J. Wan Y., Rolfe B.E., et al.; Effect of Estrogen on Vascular Smooth Muscle Cells is Dependent upon Cellular Phenotype; Atherosclerosis; 1998; 140:97-104.
Lavigne M.C., Ramwell P.W., Clarke R.; Inhibition of Estrogen Receptor Function Promotes Porcine Coronary Artery Smooth Muscle Cell Proliferation; Steriods; 1999; 64: 472-80.

(Continued)

*Primary Examiner*—Jon E. Angell
*Assistant Examiner*—Amy H. Bowman
(74) *Attorney, Agent, or Firm*—Mathews, Shepherd, McKay & Bruneau, P.A.

(57) ABSTRACT

The present invention provides novel antisense oligonucleotides that target the genes and mRNAs encoding mammalian Estrogen Receptors (ER) alpha and/or beta and modulate the receptors' responses. These antisense oligonucleotides may be used alone or in combination with 17 Beta estradiol or a related compound (genistein, estradiol derivatives . . . ) to improve plaque stabilization, vascular healing and endothelial recovery after vascular injury. Also provided are methods for designing and testing the antisense oligonucleotides. Such oligonucleotides may be used to modulate the beneficial effects mediated by the ER on vascular healing, for example, restenosis or plaque stabilisation, in mammals. The present invention further pertains to pharmaceutical compositions and formulations comprising the novel antisense oligonucleotides of the present invention for use in the treatment of mammals having a disease or disorder characterised by atherosclerosis, plaque vulnerability or destabilisation or pathological plaque rupture or erosion including spontaneous or induced injury.

7 Claims, 15 Drawing Sheets

OTHER PUBLICATIONS

Akishita M., Ouchi Y., Miyoshi H. et al.; Estrogen Inhibits Cuff-Induced Intimal Thickening of Rat Femoral Arterty; Effects of Migration and Proliferation of Vascular Smooth Muscle Cells; Atherosclerosis; 1997; 130:1-10.

Lantin-Hermoso R.L., Rosenfeld C.R., Yuhanna I.S., et al.; 15 Estrogen Acutely Stimulates Nitric Oxide Synthase Activity In Fetal Pulmonary Artery Endothelium; Am. J. Physiol.; 1997; 2731119-26.

Herrington D.; Role of Estrogens, Selective Estrogen Receptor Modulators and Phytoestrogens in Cardiovascular Protection; Can. J. Cardiol.; 2000; 16 Suppl. E:5E-9E.

Cenci S., Weitzmann M.N., Roggia C., et al.; Estrogen Deficiency Induces Bone Loss by Enhancing T-cell Production of TNF-alpha; J. Clin. Invest.; 2000-106:1229-37.

Silbiger S., Lei J., Ziyadeh, F.N., et al.; Estradiol Reverses TGF-beta1-stimulated Type IV Collagen Gene Transcription in Murine Mesangial Cells; Am. J. Physiol.; 1998; 274:FI 113-8.

Chandrasekar B., Tanguay, J.F.; Local Delivery of 17-beta-estradiol Decreases Neointimal Hyperlasia After Coronary Angioplasty in a Porcine Model; J. Am. Coll. Cardiol; 2000; 36:1972-8.

Mendelsohn, M.E., Karas, R.H.; The Protective Effects of Estrogen on the Cardiovascular System; N. Engl. J. Med.; 1999; 340: 180111.

Hayashi, K., Takahashi, M. Kirura, K., et al.; Changes in the Balance of Phosphoinositide 3-Kinase/protein Kinase B (Akt) and the Mitogen-Activated Protein Kinases (ERK/p38MAPK) determine a phenotype of visceral and Vascular Smooth Muscle Cells; J. Cell. Biol.; 1999; 145:727-40.

Simoncini, T., Genazzani, A.R.; Direct Vascular Effects of Estrogens and Selective Estrogen Receptor Modulators; Curr. Opin. Obstet. Gynecol.; 2000; 12; 12:181-7.

Finking G., Krauss N., Romer S., et al., 17-beta-estradiol, Gender Independently, Reduces Atheroma Development But Not 20 Neointimal Proliferation After Balloon Injury in the Rabbit Aorta; Atherosclerosis; 2001; 154:39-49.

Clarke S.C., Schofield P.M., Grace A.A., et al.; Tamoxifen Effects on Endothelial Function and Cardiovascular Risk Factors In Men With Advanced Atherosclerosis Circulation; 2001; 103:1497-502.

Van Baal W.M., Kenemans P., Emeis J.J., et al.; Longterm Effects of Combined Hormone Replacement Therapy on Markers of Endothelial Function and Inflammatory Activity in Healthy Postmenopausal Women; Fertil. Steril.; 1999; 71:663-70.

Sader M.A., McCredie R.J., Griffiths K.A., et al.; Oestradiol Improves Arterial Endothelial Function in Healthy Men Receiving Testosterone; Clin. Endocrinol (Oxf).; 2001; 54:175-81.

Shaul P.W.; Novel Role of Estrogen Receptors in Vascular Endothelium; Semin. Perinatol; 2000; 24:70-4.

Razandi M., Pedram A., Levin E.R.; Estrogen Signals to the Preservation of Endothelial Cell Form and Function; J. Biol. Chem.; 2000; 275:38540-6.

Giguere V., Tremblay A., Tremblay G.B.; Estrogen Receptor Beta: Re-evaluation of Estrogen and Antiestrogen Signaling; Steroids; 1998; 63:335-9.

Brzozowski A.M., Pike A.C., Dauter Z., Hubbard R.E., Bonn T., Engstrom O., Ohman L., Greene G.L., Gustafsson J.A., Cariquist M.; Molecular Basis of Agonism and Antagonism in the Oestrogen Receptor; Nature; 1997; 389:753-8.

Evans M.J., Harris H.A., Miller C.P., Karathanasis S.K., Adelman S.J.; Estrogen Receptors Alpha and Beta Have Similar Activities in Multiple Endothelial Cell Pathways; Endocrinology; 2002; 143:3785-95.

Grodstein F., Manson J.E., Stampfer M.J.; Postmenopausal Hormone Use and Secondary Prevention of Coronary Events in the Nurses' Health Study—A Prospective, Observational Study; Ann. Intern. Med.; 2001; 135:1-8.

Nelson H.D., Humphrey L.L., Nygren P., Teutsch S.M., Allan J.D.; Postmenopausal Hormone Replacement Therapy: Scientific Review; Jama; 2002; 288:872-81.

Koh K.K.; Effects of Estrogen on the Vascular Wall: Vasomotor Function and Inflammation; Cardiovasc. Res.; 2002 55:714-26.

Keshamounl V.G., Mattingly R.R., Reddy K.B.; Mechanism of 17-beta-estradiol-induced Erk1/2 Activation in Breast Cancer Cells—A Role for HER2 and PKC-delta; J. Biol. Chem.; 2002; 277:22558-65.

Mendelsohn M.E.; Mechanisms of Estrogen Action in the Cardiovascular System; J. Steroid Biochem. Mol. Biol.; 2000; 74:337-43.

Luconi M., Forti G., Baldi E.; Genomic and Nongenomic Effects of Estrogens: Molecular Mechanisms of Action and Clinical Implications for Male Reproduction; J. Steroid Biochem. Mol. Biol.; 2002; 80:369-81.

Pare G., Krust A., Karas R.H., Dupont S., Aronovitz M., Chambon P., Mendelsohn M.E.; Estrogen Receptor-Alpha Mediates the Protective Effects of Estrogen Against Vascular Injury; Circ. Res.; 2002; 90:1087-92.

Simoncini T. Fornari L., Mannella P., Varone G., Caruso A., Liao J.K., Genazzani A.R.; Novel Non-transcriptional Mechanisms for Estrogen Receptor Signaling in the Cardiovascular System—Interaction of Estrogen Receptor Alpha With Phosphatidylinositol 3-OH kinase; Steriods; 2002; 67:935-9.

Zhu Y., Bian Z., Lu P., Karas R.H., Bao L., Cox D., Hodgin J., Shaul P.W., Thoren P., Smithies O., Gustafsson J.A., Mendelsohn M.E.; Abnormal Vascular Function and Hypertension in Mice Deficient in Estrogen Receptor Beta; Science.; 2003; 295:505-8.

Chandrasekar B., Tanguay J.F.; Local Delivery of 17-Beta-estradiol Decreases Neointimal Hyperplasia After Coronary Angioplasty in a Porcine Model; J. Am. Coll. Cardiol.; 2000; 36:1972-8.

Chandrasekar B., Nattel S., Tanguay J.F.; Coronary Artery Endothelial Production After Local Delivery of 17-Beta-estradiol During Balloon Angioplasty in a Porcine Model: A Potential New Pharmacologic Approach to Improve Endothelial Function; J. Am. Coll. Cardiol.; 2001; 38:1570-6.

Inamdar S.R., Eyster K.M., Schlenker E.H.; Estrogen Receptor-Alpha Antisense Decreases Brain Estrogen Receptor Levels and Affects Ventilation in Male and Female Rats; J. Appl. Physiol.; 2001; 91:1886-92.

Geraldes P., Sirois M.G., Bernatchez P.N., Tanguay J.F.; Estrogen Regulation of Endothelial and Smooth Muscle Cell Migration and Proliferation: Role of p38 and p42/44 Mitogen-Activated Protein Kinase; Arterioscler Thormb. Vasc. Biol.; 2002; 22:1585-90.

Arnal J.F., Bayard F.; Alteration in Endothelial Estrogen Receptor Expression: A Potential Key of Vasculoprotection By Estrogens?; Circ. Res.; 2002; 91:759-60.

Lazennec G., Alcorn J.L., Katzenellenbogen B.S.; Adenovirus-Mediated Delivery of a Dominant Negative Estrogen Receptor Gene Abrogates Estrogen-Stimulated Gene Expression and Breast Cancer Cell Proliferation; Mol. Endocrinol.; 1999; 13:969-80.

Stein C.A.; Does Antisense Exist?; Nat. Med.; 1995; 1:1119-21.

Liu M.M., Albanese C., Anderson C.M., Hilty K., Webb P., Uht R.M., Price R.H., Jr., Pestell R.G., Kushner P.J.; Opposing Action of Estrogen Receptors Alpha and Beta on Cyclin D1 Gene Expression; J. Biol. Chem.; 2002; 277:24353-60.

Levin E.R.; Cellular Functions of Plasma Membrane Estrogen Receptors; Steroids; 2002; 67:471-5.

Makela S., Savolainen H., Aavik E., Myllarniemi M., Strauss L., Taskinen E., Gustafsson J.A., Hayry P.; Differentiation Between Vasculoprotective and Uterotrophic Effects of Ligands With Different Binding Affinities to Estrogen Receptors Alpha and Beta; Proc. Natl. Acad. Sci. USA; 1999; 96:7077-82.

Brouchert L., Krust A., Dupont S., Chambon P., Bayard F., Arnal J.F.; Estradiol Accelerates Reendothelialization in Mouse Carotid Artery Through Estrogen Receptor-Alpha but not Estrogen Receptor-Beta; Circulation; 2001; 103:423-8.

Haynes M.P., Sinha D., Russell K.S., Collinge M., Fulton D., Morales-Ruiz M., Sessa W.C., Bender J.R.; Membrane Estrogen Receptor Engagement Activates Endothelial Nitric Oxide Synthase Via the P13-kinase-Akt Pathway in Human Endothelial Cells; Circ. Res.; 2000; 87:677-82.

Song R.X., McPherson R.A., Adam L., Bao Y, Shupnik, M., Kumar R., Santen R.J.; Linkage of Rapid Estrogen Action to MAPK Activation by ERalpha-Shc Association with Shc Pathway Activation; Mol. Endocrinol.; 2002; 16:116-27.

Lu Q., Ebling H., Mittler J., Baur W.E., Karas R.H.; MAP Kinase Mediates Growth Factor-Induced Nuclear Translocation of Estrogen Receptor Alpha; FEBS Lett.; 2002; 516:1-8.

Darblade B., Pendaries C., Krust A., Dupont S., Fouque M.J., Rami J., Chambon P., Bayard F., Arnal J.F.; Estradiol Alters Nitric Oxide Production in the Mouse Aorta Through the Alpha-, But Not Beta-, Estrogen Receptor; Circ. Res.; 2002; 90:413-9.

Turner, S.W.P. et al, "Confinement-Induced Entropic Recoil of Single DNA Molecules in a Nanofluidic Structure," Physical Review Letters, vol. 88, No. 12, Mar. 25, 2002, pp. 128103-1 to 128103-4.

Taylor, A H et al., "Specific inhibition of estrogen receptor alpha function by antisense oligodeoxyribonucleotides", Antisense & Nucleic Acid Drug Development, Mary Ann Liebert, Inc, New York US vol. 11 No. 4 Aug. 2001 pp. 219-231.

McInerney, E M et al., "Transcription activation by the human estrogen receptor subtype beta (erbeta) studied with ERbeta and ERalpha receptor chimeras", Endocrinology, vol. 139, No. 11, Nov. 1998 pp. 171-184.

* cited by examiner

A

| | | | | | |
|---|---|---|---|---|---|
| p-p44 MAPK-<br>p-p42 MAPK- |  | | | | |
| Expression (%) | 100 | 412 | 121 | 65 | 36 |
| PDGF-BB<br>(10ng/ml) | − | + | + | + | + |
| Time-treatment | PBS | 5min | 10min | 15min | 30min |

B

| | | | | | | |
|---|---|---|---|---|---|---|
| p-p44 MAPK-<br>p-p42 MAPK- |  | | | | | |
| Expression (%) | 100 | 216 | 152 | 129 | 90 | 82 |
| PDGF-BB<br>(10ng/ml; 5 min) | − | + | + | + | + | + |
| 17βE ($10^{-8}$ M) | − | − | + | + | + | + |
| Time-treatment | PBS | 5min | 5min | 10min | 15min | 30min |

C

| | | | | | | |
|---|---|---|---|---|---|---|
| p-p44 MAPK-<br>p-p42 MAPK- |  | | | | | |
| Expression (%) | 100 | 702 | 209 | 457 | 598 | 793 |
| PDGF-BB<br>(10ng/ml; 5 min) | − | + | + | + | + | + |
| 17βE ($10^{-8}$ M) | − | − | + | + | + | + |
| Tam ($10^{-7}$M) | − | − | − | + | − | − |
| 4OHT ($10^{-7}$M) | − | − | − | − | + | − |
| Ral ($10^{-7}$M) | − | − | − | − | − | + |

A

| p-p38 MAPK- | | | | | |
|---|---|---|---|---|---|
| Expression (%) | 100 | 135 | 136 | 130 | 185 |
| PDGF-BB (10ng/ml) | − | + | + | + | + |
| Time-treatment | PBS | 5min | 10min | 15min | 30min |

B

| p-p38 MAPK- | | | | | | |
|---|---|---|---|---|---|---|
| Expression (%) | 100 | 187 | 114 | 127 | 67 | 70 |
| PDGF-BB (10ng/ml; 30 min) | − | + | + | + | + | + |
| 17βE ($10^{-8}$ M) | − | − | + | + | + | + |
| Time-treatment | PBS | 5min | 5min | 10min | 15min | 30min |

C

| p-p38 MAPK- | | | | | | |
|---|---|---|---|---|---|---|
| Expression (%) | 100 | 235 | 119 | 176 | 180 | 156 |
| PDGF-BB (10ng/ml; 30 min) | − | + | + | + | + | + |
| 17βE ($10^{-8}$ M) | − | − | + | + | + | + |
| Tam ($10^{-7}$M) | − | − | − | + | − | − |
| 4OHT ($10^{-7}$M) | − | − | − | − | + | − |
| Ral ($10^{-7}$M) | − | − | − | − | − | + |

| p-p44 MAPK-<br>p-p42 MAPK- |  | | | | |
|---|---|---|---|---|---|
| Expression (%) | 100 | 1122 | 1074 | 1420 | 1835 |
| Time-treatment | PBS | 5min | 10min | 15min | 30min |
| 17βE ($10^{-8}$ M) | − | + | + | + | + |

B

| p-p44 MAPK-<br>p-p42 MAPK- |  | | | | |
|---|---|---|---|---|---|
| Expression (%) | 100 | 630 | 437 | 396 | 281 |
| 17βE ($10^{-8}$ M) | − | + | + | + | + |
| Tam ($10^{-7}$M) | − | − | + | − | − |
| 4OHT ($10^{-7}$M) | − | − | − | + | − |
| Ral ($10^{-7}$M) | − | − | − | − | + |

A

| p-p38 MAPK- | | | | | |
|---|---|---|---|---|---|
| Expression (%) | 100 | 107 | 124 | 121 | 215 |
| Time-treatment | PBS | 5min | 10min | 15min | 30min |
| 17βE ($10^{-8}$ M) | − | + | + | + | + |

B

| p-p38 MAPK- | | | | | |
|---|---|---|---|---|---|
| Expression (%) | 100 | 208 | 117 | 121 | 102 |
| 17βE ($10^{-8}$ M) | − | + | + | + | + |
| Tam ($10^{-7}$M) | − | − | + | − | − |
| 4OHT ($10^{-7}$M) | − | − | − | + | − |
| Ral ($10^{-7}$M) | − | − | − | − | + |

Figure 8

ANTISENSE STRATEGY TO MODULATE ESTROGEN RECEPTOR RESPONSE (ER α AND/OR ER β )

FIELD OF THE INVENTION

The present invention pertains to the field of antisense oligonucleotides for mammalian estrogen receptor (ER) genes and their use as cardioprotective, vascular healing and/or anti-atherosclorotic agents.

BACKGROUND OF THE INVENTION

Atherosclerosis is a process by which new lesions can progress or become vulnerable from pre-existing ones, and can be summarised as the culmination of i) increased endothelial cell dysfonction; ii) migration of inflammatory cells into extracellular matrix; iii) synthesis and release of degrading matrix molecules; iv) fibrous cap thinning, erosion and/or rupture; v) release of growth factors; vi) prothrombotic, proinflammatory, proapoptotic and/or proatherosclerotic status. Physiological vascular healing and regeneration are highly coordinated processes that occur in individuals under specific conditions, such as during spontaneous plaque rupture and/or destabilisation, or induced by percutaneous or surgical revascularization.

Estrogens play an important role in bone maintenance, in the cardiovascular system, in the growth, differentiation and biological activity of various tissues[1]. The protective effects of 17-beta-estradiol (17βE) are related to favourable changes in plasma lipid profile[2], to inhibition of vascular smooth muscle cell (VSMC) proliferation[3] and migration[4], to relaxation of coronary vessels through endothelial nitric oxide synthase (eNOS) activity[5], to reduction of platelets and monocyte aggregation[6], tumor necrosis factor alpha (TNF-a) release[7] and extracellular matrix synthesis[8]. We have shown that local delivery of 17βE reduces neointimal thickness after coronary balloon injury in a porcine model[8].

Estrogen can bind to two estrogen receptors (ER), alpha (ERα) and beta (ERβ), which are expressed in all vascular cells types[10]. The classical genomic mechanism, or long-term effect of estrogen on vascular tissues, is dependent on change in gene expression in the vascular tissues. Most recently, a second mechanism with direct (or nongenomic) estrogen effect has been identified[11]. Administration of estrogen can induce a rapid effect suggesting that its activities are linked to the induction of other intracellular pathways such as the mitogen-activated protein kinases (MAPKs)[11]. The MAPKs, which are involved in the proliferation, migration and differentiation of VSMC, are stimulated in rat carotid arteries after endothelial injury[12]. Treatment with estrogen may influence the MAPK pathway in a variety of cell types and may provide protection against vascular injury.

As indicated above, the major effects of estrogens are mediated through the two distinct estrogen receptors, ERα and ERβ. Each of these ER is encoded by a unique gene[19] with some degree of homology between each other, and the genes are organized into six domains (A to F)[10]. The amino-terminal A-B domain represents the ligand-independent transcriptional-activation function 1 (TAF-1). The ER have only 18% of homology in this amino-terminus domain. The C domain, which represents the DNA binding domain, is extremely conserved in all steroid receptors and domain D contains the hinge region of the ER. The hormones bind the E domain which also contains a ligand-dependent transcriptional-activation function 2 (TAF-2). The two ER have 97% and 60% homology in domains C and E, respectively. The carboxy-terminal F domain is a variable region and it has been proposed that the F domain may play an important role in the different responses of ER to 17-beta-estradiol or selective ER modulators[20]. The expression pattern of the two ER are very different in many tissues and may suggest distinct responses in the presence of 17-beta-estradiol. Three studies with transgenic knock-out (KO) mice were done and the treatment with 17-beta-estradiol, in the absence of one of two ER (αERKO and βERKO) or both ER (αβERKO) prevented the hyperplasia formation after carotid injury.

SUMMARY OF THE INVENTION

Until now there has been no data on the specific effects of each ER on the different vascular cell types which are the endothelial cells and the smooth muscle cells. Based on our findings, optimizing the beneficial effects of 17-beta-estradiol in vascular healing and endothelial recovery after vascular injury by selectively inhibiting the expression of one receptor or both receptors is envisageable.

We examined the activity of 17βE on endothelial and smooth muscle cell proliferation and migration with or without estrogen antagonists. Furthermore, we studied the action of estrogen on p42/44 and p38 MAPK activity that are believed to play a role on proliferation and migration signal transduction pathways of endothelial and smooth muscle cells.

We present hereinbelow evidence of a differential effect of 17 β-estradiol on two different vascular cell types: endothelium and muscle. The results below give more strength to the principles at the basis of this invention: antisense technology directed against estrogen receptors ERα and/or ERβ would be an advantageous alternative over the simple use of a ligand to these receptors in modulating their responses. This antisense gene therapy could be used to selectively block the synthesis of a specific ER receptor and, by removing a potential negative feed-back loop, could potentiate the positive effects of estrogens.

ER cDNAs have been cloned (Gene Bank-Z37167 and AF267736) and we synthesized two oligonucleotide phosphorothiorate backbone sequences to each ER (antisense 1, AS1-ERα: CTC GTT GGC TTG GAT CTG (SEQ ID NO:1), nucleotides 49 through 67; AS2-ERβ: GAC GCT TTG GTG TGT AGG (SEQ ID NO:2), nucleotides 12 through 30; AS1-ERβ: GTA GGA GAC AGG AGA GTT (SEQ ID NO:3), nucleotides 31 to 49; AS2-ERβ: GCT AAA GGA GAG AGG TGT (SEQ ID NO:4), nucleotides 243 to 261). These four antisenses correspond to a sequence of ER domain A-B, wherein less homology is found between the two ER. With these antisense molecules or modified versions, it has been possible to characterize the effects of each ER on many cells (in particular, endothelial and smooth muscle cells) in order to develop a new therapy to improve vascular healing and cardioprotection.

An object of the present invention is therefore to provide anti-destabilisation and/or pro-vascular healing antisense oligonucleotides directed toward mammalian estrogen receptors and uses thereof. In accordance with an aspect of the present invention, there is provided an antisense oligonucleotide complementary to a gene encoding a mammalian estrogen receptor (ER) selected from the group comprising ER alpha and ER beta, wherein said antisense oligonucleotide comprises about 15 to about 25 nucleotides complementary to said gene.

In accordance with another aspect of the invention, there is provided a pharmaceutical composition comprising a pharmaceutically acceptable diluent and an antisense oligonucleotide complementary to a gene encoding a mammalian estrogen receptor selected from the group comprising ER alpha and ER beta, wherein said antisense oligonucleotide comprises about 15 to about 25 nucleotides complementary to said gene and wherein the ER is a non-porcine receptor.

In accordance with another aspect of the invention, there is provided a method of blocking pathological vascular injury or vulnerability in a mammal in need of such therapy, comprising the step of administering to said mammal an antisense oligonucleotide complementary to a gene encoding a mammalian ER selected from the group comprising ER alpha and/or ER beta.

In accordance with another aspect of the invention, there is provided a method of improving vascular healing in a mammal in need of such therapy, comprising the step of administering to said mammal the antisense oligonucleotide an antisense oligonucleotide complementary to a gene encoding a mammalian ER selected from the group comprising ER alpha and ER beta.

The effective regulation of pathological plaque vulnerability, injury and healing using the antisense oligonucleotides of the present invention can be useful in medical treatments for various diseases and disorders including, but not limited to, atherosclerosis, inflammation, plaque destabilisation, vascular injury and restenosis.

Moreover, antisense technology is emerging as an effective means for blocking or inhibiting the expression of specific gene products and, therefore, can be uniquely useful in a number of therapeutic, diagnostic, and research applications involving the modulation of estrogen receptor expression.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 4: Porcine smooth muscle cells (PSMC) were rinsed and stimulated A) with platelet derived growth factor-BB (PDGF-BB) for 5 to 30 min B) treated with 17-beta-estradiol (17βE) for 5 to 30 min and then stimulated with PDGF-BB for 30 min C) pretreated 5 min with Tamoxifen (Tam), 4-OH-Tamoxifen (4-OHT) and Raloxifen (Ral) and added with 17βE ($10^{-8}$ M) for 30 min and then stimulated with PDGF-BB for 30 min. Proteins were detected by Western Blot analysis. Image densitometry results are given as relative expression (%) as compared with PBS-treated cells.

FIG. 8: Porcine aortic endothelial cells (PAEC) were rinsed and stimulated A) with 17βE for 5 to 30 min B) pre-treated 5 min with Tamoxifen (Tam), 4-OH-Tamoxifen (4-OHT) and Raloxifen (Rai) and then stimulated with 17βE for 30 min. Proteins were detected by Western Blot analysis. Image densitometry results are given as relative expression (%) as compared with PBS-treated cells.

DETAILED DESCRIPTION OF THE INVENTION

Figure 1:
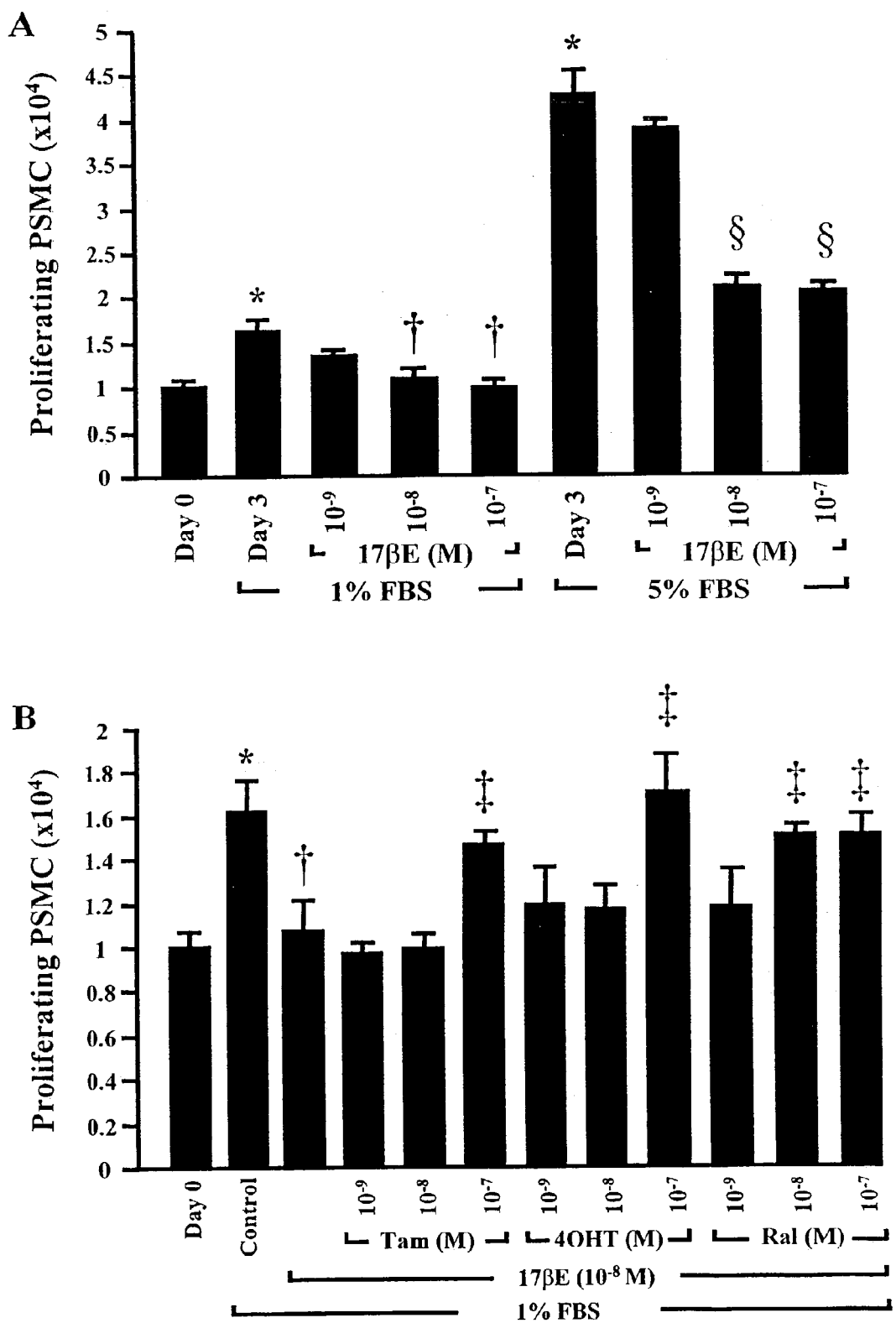
FIG. 1: Porcine smooth muscle cells (PSMC) were seeded at $1 \times 10^4$ cells/well and stimulated as described in methods. A) The cells were then stimulated with 17-beta-estradiol (17βE) B) combine treated with Tamoxifen (Tam), 4-OH-Tamoxifen (4-OHT) or Raloxifen (Ral). The values are means of cell count obtained from six wells for each treatment. *, $p<0.05$ as compared to day 0; †, $p<0.05$ as compared to 5 control; §, $p<0.05$ as compared to 17βE ($10^{-8}$ M).

The present invention employs antisense oligonucleotides for use in modulating the function of nucleic acid molecules encoding estrogen receptors (ER) alpha and beta, ultimately modulating the amount of ER protein produced. This is accomplished by providing antisense compounds which specifically hybridise with one or more nucleic acids encoding estrogen receptors alpha and beta. The overall effect of such interference with target nucleic acid function is modulation of the expression of estrogen receptors (ER), ER-alpha and/or ER-beta.

Antisense compounds are commonly used as research and diagnostic reagents. For example, antisense oligonucleotides, which are able to inhibit gene expression with exquisite specificity, are often used by those of ordinary skill in the relevant art to elucidate the function of particular genes. Antisense compounds are also used, for example, to distinguish between functions of various members of a biological pathway. Antisense modulation has, therefore, been harnessed for research use. The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic agents that can be configured to be useful for the treatment of cells, tissues and animals, especially humans.

We therefore propose a new therapeutic strategy to treat an injured or vulnerable atherosclerotic vessel with antisense to ERα and/or ERβ alone or in combination with 17-beta-estradiol or a related compound (genistein, estradiol derivatives . . . ) in order to optimize the effects on vascular healing and endothelial recovery after vascular injury. The antisense, alone or in combination with a specific dose of 17-beta-estradiol, will improve vascular healing and endothelial recovery after vascular injury and will bring a new, innovative therapy with application not limited to cardiovascular angioplasty but in other areas of the body (cerebral, renal, peripheral vasculature . . . ) wherein estrogens have an effect.

DEFINITIONS

Unless defined otherwise, all technical and scientific terms used herein have the same meaning as commonly understood by one of ordinary skill in the art to which this invention belongs.

"Antisense", as used herein, refers to the specific hybridisation of an oligonucleotide with its target nucleic acid so as to interfere with the normal function of the nucleic acid. This modulation of function of a target nucleic acid by compounds which specifically hybridise to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA.

"Antisense oligonucleotide", as used herein, refers to any oligonucleotide that is complementary to the target gene. The antisense oligonucleotide may be in the form of DNA, RNA or any combination thereof.

"Corresponds to" refers to a polynucleotide sequence is homologous (i.e., is identical, not strictly evolutionarily related) to all or a portion of a reference polynucleotide sequence, or that a polypeptide sequence is identical to a reference polypeptide sequence.

In the context of this invention, "hybridisation" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucle otide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridisable" and, "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridisable. An antisense compound is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

"Naturally-occurring", as used herein, as applied to an object, refers to the fact that an object can be found in nature. For example, a polypeptide or polynucleotide sequence that is present in an organism (including viruses) that can be isolated from a source in nature and which has not been intentionally modified in the laboratory is naturally-occurring.

"Nucleic acid" refers to DNA and RNA and can be either double stranded or single stranded. The invention also includes nucleic acid sequences which are complementary to the claimed nucleic acid sequences.

"Oligonucleotide", as used herein, refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

For oligonucleotides, examples of pharmaceutically acceptable salts include but are not limited to (a) salts formed with cations such as sodium, potassium, ammonium, magnesium, calcium, polyamines such as spermine and spermidine, etc., (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

"Polynucleotide" refers to a polymeric form of nucleotides of at least 10 bases in length, either ribonucleotides or deoxynucleotides or a modified form of either type of nucleotide. The term includes single and double stranded forms of DNA or RNA.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 to Imbach et al.

"Protein", as used herein, refers to a whole protein, or fragment thereof, such as a protein domain or a binding site for a second messenger, co-factor, ion, etc. It can be a peptide or an amino acid sequence that functions as a signal for another protein in the system, such as a proteolytic cleavage site.

An expression vector comprising the antisense oligonucleotide sequence may be constructed having regard to the sequence of the oligonucleotide and using procedures known in the art.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Other biochemistry and chemistry terms herein are used according to conventional usage in the art, as exemplified by The McGraw-Hill Dictionary of Chemical Terms (ed. Parker, S., 1985), McGraw-Hill, San Francisco).

DESCRIPTION OF EMBODIMENTS

In one embodiment of the present invention, antisense oligonucleotides are designed that are complementary to specific regions of mammalian ER-alpha and ER-beta genes. In a specific embodiment of the present invention antisense oligonucleotides are designed that are complementary to specific regions of the human ER-alpha and ER-beta genes.

Exemplary antisense oligonucleotide sequences of the present invention are listed below. It should be apparent to one skilled in the art that other antisense oligonucleotide sequences that are complementary to specific regions of mammalian ER-alpha and ER-beta genes are within the scope of the present invention.

```
PORCINE ER-alpha

AS1-ERalpha:    5'-CTC GTT GGC TTG GAT CTG-3'    (SEQ ID NO:1)
AS2-ERalpha:    5'-GAC GCT TTG GTG TGT AGG-3'    (SEQ ID NO:2)
PORCINE ER-beta AS1-ERbeta:     5'-GTA GGA GAC AGG AGA GTT-3'    (SEQ ID NO:3)
AS2-ERbeta:     5'-GCT AAA GGA GAG AGG TGT-3'    (SEQ ID NO:4)
HUMAN ER-alpha AS1-ERalpha:    5'-AAC GCC GCA GCC TCA GAC-3'    (SEQ ID NO:5)
AS2-ERalpha:    5'-CCG AAC GCC GCA GCC TCA-3'    (SEQ ID NO:6)
AS3-ERalpha:    5'-GAT GCT TTG GTG TGG AGG-3'    (SEQ ID NO:7)
AS4-ERalpha:    5'-CGT TGA ACT CGT AGG CGG-3'    (SEQ ID NO:8)
HUMAN ER-beta AS1-ERbeta:     5'-AGA TGG TGA GTT TTT TAT-3'    (SEQ ID NO:9)
AS2-ERbeta:     5'-TGT AGG AGG AAG GAG AAT-3'    (SEQ ID NO:10)
AS3-ERbeta:     5'-GTT GTA GGA GGA AGG AGA-3'    (SEQ ID NO:11)
AS4-ERbeta:     5'-TAG GAG GAA GGT ATG TAT-3'    (SEQ ID NO:12)
```

Design and Preparation of Antisense Oligonucleotides

"Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a mammalian ER that is ER-alpha or beta. As used herein the "gene encoding a estrogen receptor" refers to any gene which encodes a protein that is capable of acting as an estrogen receptor. Gene sequences are often available on electronic databases, for example, GenBank. In the present invention the porcine antisense oligonucleotides were designed from the sequence in GenBank Accession Nos. NM214220 and AF164957, and the human antisense oligonucleotides were designed from the sequence in GenBank Accession Nos M12674 and AB006589.

The targeting process also includes determination of a site or sites within this gene for the antisense interaction to occur such that the desired effect, e.g., detection or modulation of expression of the protein, will result. Within the context of the present invention, a possible intragenic site is the region encompassing the translation initiation or termination codon of the open reading frame (ORF) of the gene. It is known in the art that eukaryotic and prokaryotic genes may have two or more alternative start codons, any one of which may be utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a mammalian estrogen receptor (ER) that is ER-alpha or ER-beta, regardless of the sequence(s) of such codons.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an $N^7$-methylated guanosine residue joined to the 5'-most residue of the mRNA via a 5'-5' triphosphate linkage. The 5' cap region of an m RNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also potential targets. It has also been found that introns can be effective target regions for antisense compounds targeted, for example, to DNA or pre-mRNA.

Once one or more target sites have been identified, oligonucleotides are chosen which are sufficiently complementary to the target, i.e., hybridise sufficiently well and with sufficient specificity, to give the desired effect.

In one embodiment of the present invention the antisense oligonucleotides are selected to have the following characteristics:

i) no more than three, or preferably less, consecutive guanosines;
ii) incapacity to form hairpin structures;
iii) minimal capacity to form homodimers; and
iv) contain between about 15 and about 25 nucleotides that are complementary to the target gene.

The antisense oligonucleotides can be selected, based on the above characteristics, using commercially available computer software, for example OLIGO® Primer Analysis.

While antisense oligonucleotides are one form of antisense compounds, the present invention contemplates other oligomeric antisense compounds, including but not limited to oligonucleotide mimetics such as are described below. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Alternative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Alternative modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In alternative oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat Nos.: 5,539,082; 5,714,331; and 5,719,262. Further teaching of PNA compounds can be found in Nielsen et al(1991) *Science,* 254, 1497–1500.

Modified oligonucleotides may also contain one or more substituted sugar moieties. For example, oligonucleotides may comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_n\ O]_m\ CH_3$, $O(CH_2)_nOCH_3$, $O(CH_2)_n\ NH_2$, $O(CH_2)_n\ CH_3$, $O(CH_2)_n\ ONH_2$, and $O(CH_2)_nON[(CH_2)_n\ CH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

Other modifications include 2'-methoxy (2'-O—$CH_3$), 2'-aminopropoxy (2'-$OCH_2CH_2\ CH_2\ NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al (1991) *Angewandte Chemie, International Edition,* 30, 613, and those disclosed by Sanghvi, Y. S., Chapter 15, Antisense Research and Applications, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278), even more particularly when combined with 2'-O-methoxyethyl sugar modifications.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al (1989) *Proc. Natl. Acad. Sci. USA,* 86, 6553–6556), cholic acid (Manoharan et al (1994) *Bioorg. Med. Chem. Lett.,* 4, 1053–1060), a thioether, e.g., hexyl-S-tritylthiol (Manoharan et al (1992) *Ann. N.Y. Acad. Sci.,* 660, 306–309; Manoharan et al (1993) *Bioorg. Med. Chem. Lett.,* 3, 2765–2770), a thiocholesterol (Oberhauser et al (1992) *Nucl. Acids Res.,* 20, 533–538), an aliphatic chain, e.g., dodecandiol or undecyl residues (Saison-Behmoaras et al(1991) *EMBO J.,* 10,1111–1118), a phospholipid, e.g., di-hexadecyl-rac-glycerol or triethylammonium 1,2-di-O-hexadecyl-rac-glycero-3-H-phosphonate (Manoharan et al (1995) *Tetrahedron Lett.,* 36, 3651–3654; Shea et al (1990) *Nucl. Acids Res.,* 18, 3777–3783), a polyamine or a polyethylene glycol chain (Manoharan et al (1995) *Nucleosides & Nucleotides,* 14, 969–973), or adamantane acetic acid (Manoharan et al (1995) *Tetrahedron Lett.,* 36, 3651–3654), a palmityl moiety (Mishra et al (1995) *Biochim. Biophys. Acta,* 1264, 229–237), or an octadecylamine or hexylamino-carbonyl-oxycholesterol moiety (Crooke et al (1996) *J. Pharmacol. Exp. Ther.,* 277, 923–937.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides may contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

Testing Activity of Antisense Oligonucleotides

One embodiment of the present invention provides methods for testing the activity of the antisense oligonucleotides. Commonly the antisense oligonucleotides are first tested in vitro to determine modulation of estrogen receptor expression and the subsequent effect of this modulation. The oligonucleotides can then be tested using in vivo techniques, using animal models, prior to their testing and subsequent use in humans.

In Vitro Assays

The in vitro assays can be performed using cultures of any cell line that expresses the alpha and/or beta estrogen receptors. For example, porcine aortic endothelial cells (PAEC) and/or smooth muscle cells (SMC) can be used to test porcine antisense oligonucleotides of the present invention and human umbilical vein endothelial cells (HUVEC) and/or SMC can be used to test human antisense oligonucleotides of the present invention. (See FIGS. 1–2, 5–6, 10–11 and 13–14.)

Various assays can be performed using cell cultures including those used to determine protein expression from the target ER-alpha and/or ER-beta genes and the downstream effects of decreased protein expression.

Western blot and/or immunohistochemical analysis of ER-alpha and ER-beta protein expression can be carried out using standard techniques and antibodies specific for ER-alpha or ER-beta. A decrease in protein expression, following treatment of cells in culture with the candidate antisense oligonucleotide, in comparison to untreated cells, is indicative of an effective antisense oligonucleotide. This is demonstrated in Example 1. Western blot and/or immunohistochemical analysis can also be used to determine the degree of ER-alpha and/or ER-beta phosphorylation. An effective antisense oligonucleotide will cause a decrease in phosphorylation, as demonstrated in Example 1.

Mitogenic assays can be performed to monitor endothelial cell proliferation in the presence and absence of a candidate antisense oligonucleotide. Effective antisense oligonucleotides of the present invention (i.e. those that are capable of down-regulating ERalpha and/or ERbeta protein expression) can modulate (block/inhibit or promote/increase) the mitogenic effect of 17-beta estradiol or related compounds and thereby reduce or increasing endothelial cell proliferation. These assays can be performed using standard techniques well known to those skilled in the art. One example of a mitogenic assay using PAEC cultures is provided in Example 1.

Mitogenic assays can be performed to monitor smooth muscle cell (SMC) proliferation in the presence and absence of a candidate antisense oligonucleotide. Effective antisense oligonucleotides of the present invention (i.e. those that are capable of down-regulating ERalpha and/or ERbeta protein expression) can modulate (block/inhibit or promote/increase) the mitogenic effect of 17-beta estradiol (estrogens or related compounds) and thereby reduce or increase SMC proliferation. These assays can be performed using standard techniques well known to those skilled in the art. One example of a mitogenic assay using PAEC and PSMC cultures is provided in Example 1. As indicated above, this assay can be adapted for use with any ER-alpha and/or ER-beta expressing cell lines.

Chemotactic assays can be performed to evaluate the effect of candidate antisense oligonucleotides on estrogen-mediated cell migration. Effective antisense oligonucleotides of the present invention (i.e. those that are capable of down-regulating ER-alpha and/or ER-beta protein expression) can modulate (block/inhibit or promote/increase) the chemotactic effect of 17-beta-estradiol (estrogen or related compounds) and thereby reduce or increase endothelial cells and/or SMC migration. These assays can be performed using standard techniques well known to those skilled in the art. One example of a chemotactic assay using PAEC and PSMC cultures is provided in Example 1. As indicated above, this assay can be adapted for use with any ER-alpha and/or ER-beta expressing cell lines.

Confocal microscopic analysis can also be used, according to standard techniques known in the art, to view the ER-alpha and ER-beta on endothelial cells and/or smooth muscle cells. Successful candidate antisense oligonucleotides will demonstrate reduced expression of ER-alpha and/or ER-beta and, therefore, a potential modulation of the effect of 17-beta-estradiol or related compounds on endothelial cells and/or smooth muscle cells.

Use of Antisense Oligonucleotides

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The antisense compounds of the present invention are also useful for research and diagnostics, because these compounds hybridize to nucleic acids encoding a mammalian estrogen receptor that is ER-alpha or ER-beta, enabling sandwich and other assays to easily be constructed to exploit this fact. Hybridization of the antisense oligonucleotides of the invention with a nucleic acid encoding a mammalian ER that is ER-alpha or ER-beta can be detected by means known in the art. Such means may include linkage of a fluorophore to the oligonucleotide, attachment of a reporter gene to the oligonucleotide, conjugation of an enzyme to the oligonucleotide, radiolabelling of the oligonucleotide or any other suitable detection means. Kits using such detection means for detecting the level of a mammalian estrogen receptor (ER) that is ER-alpha or ER-beta in a sample may also be prepared.

Antisense Oligonucleotide Administration

When employed as pharmaceuticals, the antisense oligonucleotides are usually administered in the form of pharmaceutical compositions. The pharmaceutical compositions are prepared by adding an effective amount of an antisense oligonucleotide to a suitable pharmaceutically acceptable diluent or carrier. As such, one embodiment of the present invention provides pharmaceutical compositions and formulations which include the antisense oligonucleotides of the invention.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Methods of delivery of foreign nucleic acids, such as antisense oligonucleotides, are known in the art, such as containing the nucleic acid in a liposome and infusing the preparation into an artery (LeClerc G. et al., (1992) *J Clin Invest.* 90: 936–44), transthoracic injection (Gal, D. et al., (1993) *Lab Invest.* 68: 18–25.). Other methods of delivery may include coating a balloon catheter with polymers impregnated with the foreign DNA and inflating the balloon in the region of arteriosclerosis, thus combining balloon angioplasty and gene therapy (Nabel, E. G. et al., (1994) *Hum Gene Ther.* 5: 1089–94.)

Another method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859. It is contemplated that the antisense oligonucleotides may be packaged in a lipid vesicle before "shotgun" delivery of the antisense oligonucleotide.

Another method of delivery involves the use of electroporation to facilitate entry of the nucleic acid into the cells of the mammal. This method can be useful for targeting the antisense oligonucleotides to the cells to be treated, for example, a tumour, since the electroporation would be performed at selected treatment areas.

In one embodiment of the present invention the antisense oligonucleotides or the pharmaceutical compositions comprising the antisense oligonucleotides may be packaged into convenient kits providing the necessary materials packaged into suitable containers.

To gain a better understanding of the invention described herein, the following examples are set forth. It should be understood that these examples are for illustrative purposes only. Therefore, they should not limit the scope of this invention in any way.

EXAMPLE 1

Role of Estrogen Receptors (ER-alpha and er-beta) on Proliferation, Migration and MAPK Pathway of Endothelial and Smooth Muscle Cells To discriminate the contribution of ER-alpha and ER-beta receptors upon endothelial cell (EC) and smooth muscle cells (SMC) stimulation by 17-beta-estradiol, selective antisense deoxyribophosphorothioate oligomers, which hybridized specifically with a complementary mRNA sequence and prevented the translation of the targeted mRNA into its protein (Crooke R., (1991) *Anticancer Drug Des.* 6, 609–646; Loke, S. et al (1989) *Proc. Natl. Acad. Sci. U.S.A.* 86, 3474–3478; Yakubov, L. A. et al (1989) *Proc. Natl. Acad. Sci. U.S.A* 86, 6454–6458), were used. This antisense gene expression knockdown approach resulted in downregulation of the protein expression of ER-alpha or ER-beta in a highly selective fashion and thus to evaluate their contribution to the biological activities mediated by 17-beta-estradiol.

The mitogenic, chemotactic and mitogen-activated-protein-kinases (MAPK) activities of 17-beta-estradiol on PAEC and PSMC were studied (see FIGS. 1–8). Furthermore, the ability of antisense oligonucleotide sequences complementary to ER-alpha or ER-beta mRNA to modulate 17-beta-estradiol-mediated effects is demonstrated (see FIGS. 9–15). We found that the effects of 17βE to promote proliferation, migration and p42/44 and p38 MAPK phosphorylation are ERα-mediated on endothelial cells in contrast to SMC in which these effects of estrogen are ERβ-mediated. These results suggest that vascular healing or other processes dependent on the estrogen receptors, ER-alpha or ER-beta can be modulated (promoted or inhibit) to favor a positive therapeutic effect.

Materials and Methods

Cell Culture

Porcine aortic endothelial cells (PAEC) and porcine smooth muscle cells (PSMC) expressing both ERα and ERβ were isolated from freshly harvested aortas, cultured in Dulbecco's modified eagle medium (DMEM; Life Technologies Inc., Carlsbad, Calif.) containing 5% fetal bovine 'serum (Hyclone Laboratories, Logan, Utah), and antibiotics (Penicillin and Streptomycin, Sigma, St-Louis, Mo.). PAEC were characterized by their cobblestone monolayer morphology. PSMC were characterized by anti-smooth muscle α-actin monoclonal antibodies and by specific morphology for SMCs.[34] PAEC and PSMC between the third and eight passage were used.

Mitogenic Assay

Confluent PAEC and PSMC were rinsed with DMEM and trypsinized. Cells were resuspended in 10 ml of DMEM, 5% FBS, and antibiotics, and a cell count was obtained with a Coulter Counter Z1 (Coulter Electronics, Luton, UK). PAEC and PSMC were seeded at $1 \times 10^4$ cells/well of 24-well tissue culture plates (Becton-Dickinson, Rutherford, N.J., U.S.A.) stimulated for 24 h in DMEM, 5% FBS, and antibiotics, and starved for 48 h in DMEM, 0.1% FBS, and antibiotics. The cells were stimulated for 72 h in DMEM, 1% or 5% FBS, antibiotics, and with or without different concentrations of 17βE (Sigma), Tamoxifen (Sigma), 40H-Tamoxifen (Sigma), Raloxifen (Eli Lilly, Indianapolis, Ind.). After trypsinization, cell number was determined by using a Coulter counter.

Chemotaxic Assay

Cell migration was evaluated using a modified Boyden 48-well microchamber kit (NeuroProbe, Cabin John, MD.). Near confluent EC and PSMC were rinsed with DMEM and trypsinized. Cells were resuspended in DMEM, 5% FBS, and antibiotics, and a cell count was obtained. PAEC and PSMC were seeded at $2.5 \times 10^5$ cells/well of six-well tissue culture plates; stimulated for 24 h in DMEM, 5% FBS, and antibiotics and starved for 48 h in DMEM, 0.1% FBS, and antibiotics with or without 17βE ($10^{-8}$M), Tamoxifen ($10^{-7}$M), 40H-Tamoxifen ($10^{-7}$M), Raloxifen ($10^{-7}$M). ER antagonists were added 5 minutes before 17βE. Cells were harvested by trypsinization and resuspended in DMEM, 1% FBS, and antibiotics at a concentration of $5 \times 10^5$ cells/ml. 50 μl of this cell suspension treated with or without 17βE ($10^{-8}$M), Tamoxifen ($10^{-7}$M), 40H-Tamoxifen ($10^{-7}$M), Raloxifen ($10^{-7}$M) was added in the higher chamber of the modified Boyden chamber apparatus, and the lower chamber was filled with DMEM, 1% FBS, antibiotics plus the desired concentration of agonist either basic fibroblast growth factor (bFGF) or platelet-derived growth factor-BB (PDGF-BB). The two sections of the system were separated by a porous polycarbonate filter (5-μm pores), pre-treated with a gelatine solution (1.5 mg/ml), and assembled. Five hours post incubation at 37° C., the nonmigrated cells were scraped with a plastic policeman, and the migrated cells were stained using a Quick-Diff solution. The filter was then mounted on a glass slide, and migrated cells were counted using a microscope adapted to a video camera to obtain a computer-digitized image.

Western Blot Analysis of p38 and p42/44 Mitogen-Activated Protein Kinase (MAPK) Phosphorylation Confluent PAEC and PSMC were starved for 7 hours in DMEM and antibiotics. Culture medium was removed, and cells were rinsed twice with ice-cold DMEM. PSMC were incubated on ice in DMEM with or without 17βE ($10^{-8}$M) for 30 min, incubated at 37° C. for 5, 10, 15 and 30 min, then brought back on ice. Cell were then rinsed with cold DMEM, incubated on ice in DMEM, bovine serum albumin (1 mg/ml), PDGF-BB (10 ng/ml) for 30 min, incubated at 37° C. for 5 min, and then brought back on ice. PAEC were incubated on ice in DMEM with or without 17βE ($10^{-7}$M) for 30 min, then incubated at 37° C. for 5, 10, 15 and 30 min and brought back on ice. For all the experiments on PSMC and PAEC, Tamoxifen ($10^{-7}$M), 40H-Tamoxifen ($10^{-7}$M), or Raloxifen ($10^{-7}$M) were added 5 min in prior to 17βE treatment. Total proteins were prepared by the addition of 500 μl of lysis buffer containing phenylmethylsulfonyl fluoride 1 mM, leupeptin 10 μg/ml, aprotinin 30 μg/ml, and NaVO$_3$ 1 mM (Sigma). Plates were incubated at 4° C. for 30 min and scraped, and the protein concentration was determined with a Bio-Rad protein kit (Bio-Rad, Hercules, Calif.). Same protein quantity for each cell type and condition were dissolved in Laemmli's buffer, boiled for 5 min in reducing conditions, separated by a 10% gradient SDS-PAGE (Protean II kit; Bio-Rad), and transblotted onto a 0.45-μm polyvinylidene difluoride membranes (Millipore Corp., Bedford, Mass.). The membranes were blocked in 5% Blotto-TTBS (5% nonfat dry milk; Bio-Rad), 0.05% Tween 20, 0.15 M NaCl, 25 mM Tris-HCl, pH 7.5) for 1 h at room temperature with gentle agitation and incubated overnight at 4° C. in 0.5% Blotto-TTBS with the addition of an anti-phospho p42/44 MAPK or an anti-phospho p38 MAPK rabbit polyclonal antiserums (α-pp42/44; dilution of 1:10 000, and α-pp38; dilution 1:5000, New England BioLabs, Beverly, Mass.). Membranes were washed with TTBS, and incubated at room temperature with an anti-rabbit IgG antibody coupled to horseradish peroxidase (dilution 1:10 000–1:20 000, Santa Cruz Biotechnology, Santa Cruz, Calif.) in 0.5% Blotto-TTBS for 30 min. Membranes were washed with TTBS, and horseradish peroxidase bound to secondary antibody was revealed by chemiluminescence (Renaissance kit, NEN Life Science Products, Boston, Mass.). Kaleidoscope molecular weight and SDS-plyacrylamide gel electrophoresis broad range marker proteins (Bio-Rad) were used as standards for SDS-plyacrylamide gel electrophoresis. Digital image densitometry (PDI Bioscience, Aurora, ON) was performed on x-ray film to determine relative percentages of p42/44 and p38 MAPK phosphorylation.

Statistical analysis—Data are mean±SEM. Statistical comparisons were performed using ANOVA followed by an unpaired Student t Test. A p value less than 0.05 was considered as significant.

Results

Effects of 17βE on PSMC Proliferation

First, we evaluated the effect of 17βE on PSMC proliferation. Stimulation of quiescent PSMC with DMEM 1% and 5% FBS increased significantly their proliferation from 10 000±714 cells/well to 16 258±1441 and 42 500±2 889 cells/well, respectively. Treatment with 17βE ($10^{-7}$M) significantly inhibited by 88% and 90% the PSMC proliferation mediated by FBS 1% and 5%, respectively (FIG. 1A). We investigated how different estrogen antagonists may interfere with 17βE activity. Treatment of quiescent PSMC with DMEM 1% FBS increased the PSMC cell count from 10 000±734 to 16 100±1 142 (FIG. 1B). A treatment with 17βE ($10^{-8}$M) inhibited completely the FBS 1% mitogenic activity (FIG. 1B). The anti-mitogenic activity of 17βE was reversed by Tam ($10^{-7}$M) and 4-OHT ($10^{-8}$M and $10^{-7}$M), and Ral ($10^{-1}$M) by 75%, 81% and 100%, respectively (FIG. 1B). In absence of 17βE, a treatment of PSMC with these ER antagonists did not alter the mitogenic activity of FBS (1%) (data not shown).

Effects of 17βE on PSMC Migration

Figure 2:
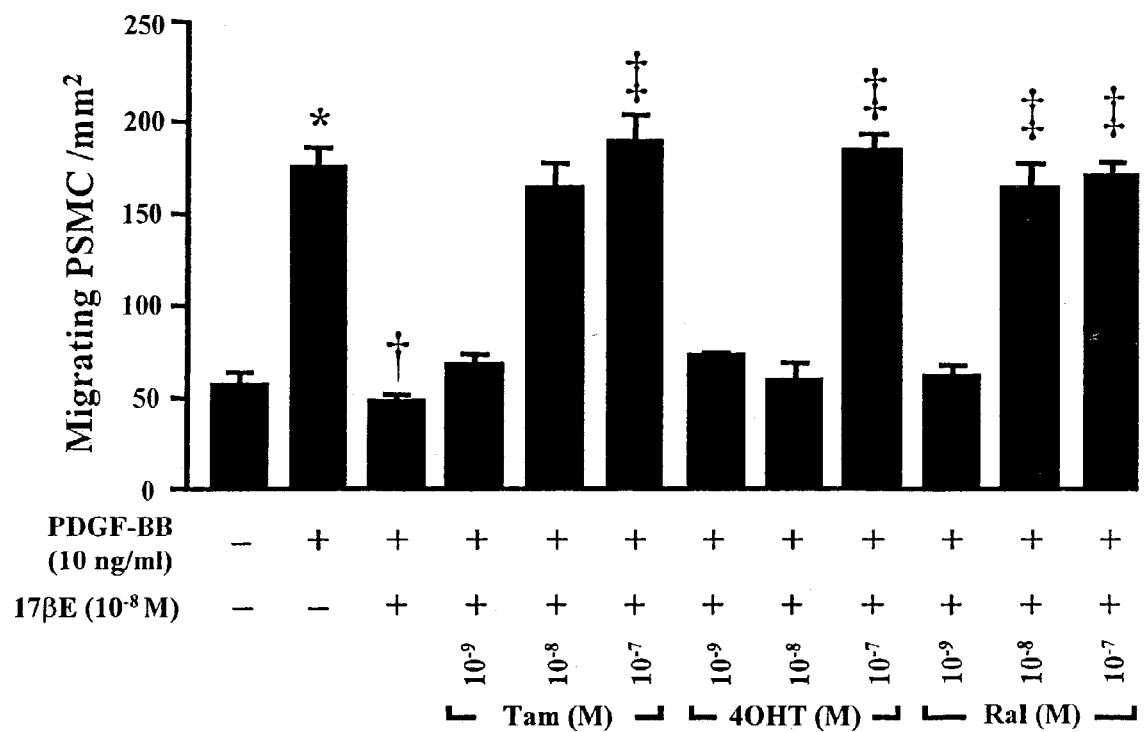
FIG. 2: Porcine smooth muscle cells (PSMC) combine treated with Tamoxifen (Tam), 4-OH-Tamoxifen (4-OHT) and Raloxifen (Ral), then treated with 17βE ($10^{-8}$ M) were added in the higher chamber of the modified Boyden chamber apparatus, the lower chamber was filled with DMEM, 1% FBS with platelet derived growth factor-BB (PDGF-BB). The values are means of migrating cells/mm$^2$ from six chambers for each treatments. *, $p<0.05$ as compared to day 0; †, $p<0.05$ as compared to control; ‡, $p<0.05$ as compared to 17βE ($10^{-8}$ M).
Figure 3:
FIG. 3: Porcine smooth muscle cells (PSMC) were rinsed and stimulated A) with platelet derived growth factor-BB (PDGF-BB) for 5 to 30 min B) treated with 17-beta-estradiol (17βE) ($10^{-8}$ M) for 5 to 30 min and then stimulated with PDGF-BB for 5 min C) pretreated 5 min with Tamoxifen (Tam), 4-OH-Tamoxifen (4-OHT) and Raloxifen (Ral) and added with 17βE for 30 min and the stimulated with PDGF-BB for 5 min. Proteins were detected by Western Blot analysis. Image densitometry results are given as relative expression (%) as compared with PBS-treated cells.
Figure 3:
Figure 3:

Using a modified Boyden chamber assay, PDGF-BB (1, 5, 10 ng/ml) induced dose-dependently and significantly the migration of PSMC by 96%, 137%, 202% as compared to DMEM 1% 5 hours post treatment (p<0.05) (data not shown). A treatment with 17βE ($10^{-8}$M) inhibited completely the chemotactic effect of PDGF-BB (10 ng/ml) (FIG. 2). In order to evaluate the interaction of ER antagonists with 17βE on PSMC chemotactic activity, PSMC were pretreated with Tam, 4-OHT and Ral ($10^{-9-10-7}$M) before adding 17βE ($10^{-8}$M). The anti-chemotactic effect of 17βE was reversed completely by Tam, 4-OHT and Ral ($10^{-7}$M) (FIG. 2). A treatment with these ER antagonists in absence of 17βE did not modify the effect of PDGF-BB on PSMC migration (data not shown).

Effects of 17βE on PSMC p42/44 and p38 MAPK Phosphorylation

Since PDGF-BB can induce SMC p42/44 and p38 MAPK phosphorylation, we investigated if a treatment with 17βE might influence the phosphorylation of these MAPK mediated by PDGF-BB. A treatment of PSMC with PDGF-BB induced a rapid and transient phosphorylation of p42/44 MAPK within 5 minutes, which decreased below the basal level within 15 minutes (FIG. 3A). Pretreatment with 17βE ($10^{-8}$M) inhibited time-dependently, with maximum inhibition at 30 minutes, the phosphorylation of p42/44 MAPK induced by 5 minutes stimulation of PDGF-BB (FIG. 3B). Pretreatment with ER antagonists ($10^{-7}$ M) added 5 min prior to the treatment with 17βE (30 min) reversed by 54%, 79% and 100% the inhibitory effect of 17βE on PDGF-BB to mediate p42/44 MAPK phosphorylation (FIG. 3C). A same series of experiment were performed on p38 MAPK phosphorylation induced by PDGF-BB. PDGF-BB (10 ng/ml) induced the phosphorylation of p38 MAPK which was maximal within 30 min as compared to PBS (FIG. 4A). Pretreatment of these cells with 17βE ($10^{-1}$M) decreased the phosphorylation of p38 MAPK mediated by PDGF-BB 30 min post stimulation in a time-dependent manner with 85% inhibition at 30 minutes (FIG. 4B). A pretreatment with Tam, 4-OHT and Ral ($10^{-7}$M) reversed by 51%, 53% and 32%, respectively the effect of 17βE (10$M) on p38 MAPK induced by 30 min stimulation of PDGF-BB (FIG. 4C). We also evaluated if a treatment with 17βE alone or ER antagonists alone had an effect on these MAPK phosphorylation. We did not observe any change in the basal phosphorylation of p42/44 and p38 MAPK on PSMC treated with 17βE alone or ER antagonists alone (data not shown).

Effects of 17βE on PAEC Proliferation

Figure 5:
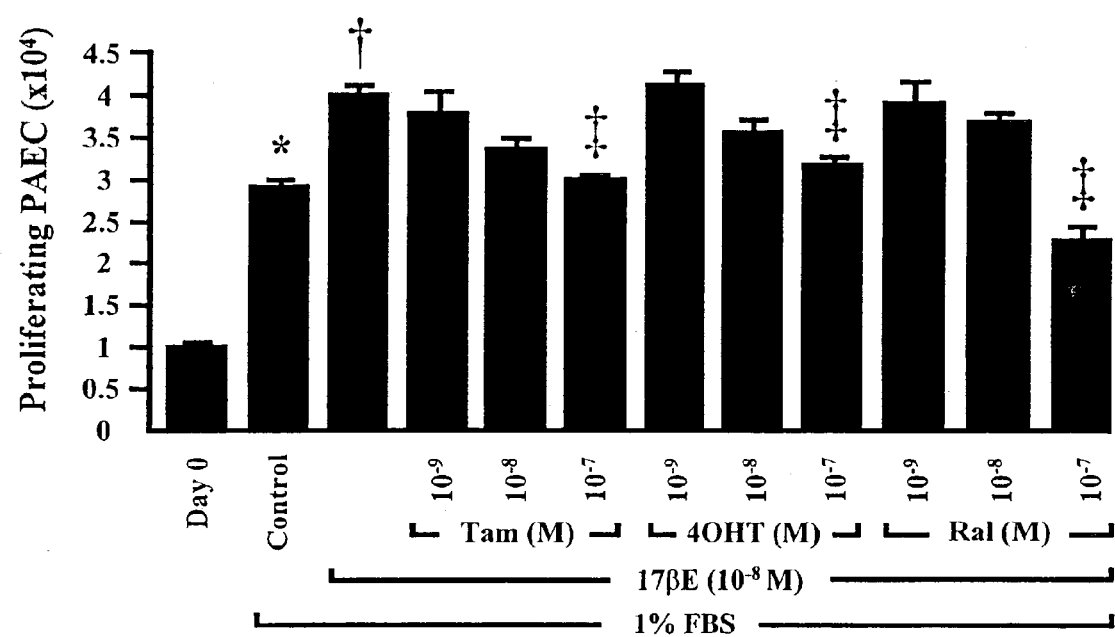
FIG. 5: Porcine aortic endothelial cells (PAEC) were seeded at $1 \times 10^4$ cells/well and stimulated as described in the methods. The cells were combine treated with 17-beta-estradiol (17βE) and Tamoxifen (Tam), 4-OH-Tamoxifen (4-OHT) or Raloxifen (Ral) in DMEM, 1% FBS. The values are means of cell counts obtained from six wells for each treatment. *, $p<0.05$ as compared to day 0; †, $p<0.05$ as compared to day 31% FBS; ‡, $P<0.05$ as compared to day 35% FBS.

Quiescent PAEC were stimulated with DMEM 1% FBS which raised basal cell count from 13 328±560 up to 24 244±843 cells/well and an addition of 17βE ($10^{-10}$ to $10^{-7}$M) induced a dose-dependent proliferation of PAEC with a maximum induction at $10^{-8}$M (data not shown). To investigate how ER antagonists may interfere with the positive effect of 17βE on endothelial cells, quiescent PAEC were stimulated with DMEM 1% FBS which raised the cell count from 10 512±832 to 29 138±870 cells/well in 72 h. A treatment of PAEC with 17βE ($10^{-8}$M) induced the proliferation of PAEC by 37% over FBS 1% treatment (FIG. 5). A pretreatment with Tam, 4-OHT and Ral ($10^{-7}$M) inhibited completely the 17βE mitogenic activity in PAEC (FIG. 5). A treatment of these cells with ER antagonists in absence of 17βE did not affect the mitogenic effect of FBS (1%) (data not shown).

Effects of 17βE on PAEC Migration

Figure 6:
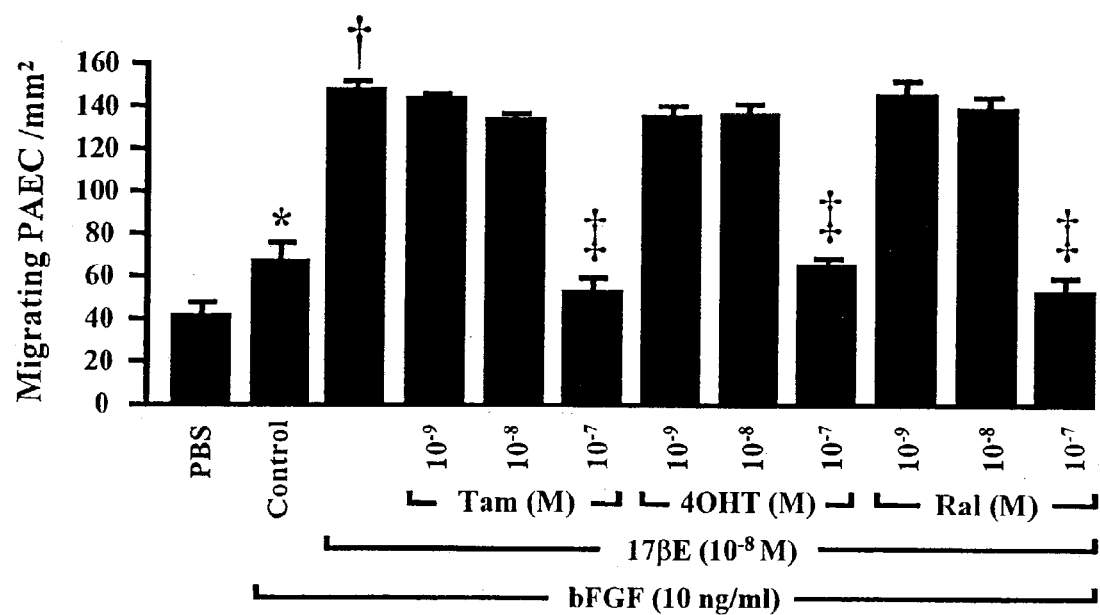
FIG. 6: Porcine aortic endothelial cells (PAEC) combine treated with 17-beta-estradiol (17βE) and Tamoxifen (Tam), 4-OH-Tamoxifen (4-OHT) or Raloxifen (Ral) were added in the higher chamber of the modified Boyden chamber apparatus, and the lower chamber was filled with DMEM, 1% FBS, with basic fibroblast growth factor (bFGF). The values are means of migrating cells/mm2 from six chambers for each treatments. *, $p<0.05$ as compared to PBS; †, $p<0.05$ as compared to bFGF (10 ng/ml); ‡, $p<0.05$ as compared to 17βE ($10^{-8}$ M).
Figure 7:
FIG. 7: Porcine aortic endothelial cells (PAEC) were rinsed and stimulated A) with 17βE for 5 to 30 min B) pre-treated 5 min with Tamoxifen (Tam), 4-OH-Tamoxifen (4-OHT) and Raloxifen (Ral) and then stimulated with 17βE for 5 min. Proteins were detected by Western Blot analysis. Image densitometry results are given as relative expression (%) as compared with PBS-treated cells.
Figure 7:

A treatment with bFGF (1, 5, 10 ng/ml) induced dose-dependently the migration of PAEC by 46%, 124%, 114% in 5 hrs as compared to DMEM 1% (p<0.05) (data not shown). In another series of experiment, a combined treatment with 17εE ($10^{-8}$M) stimulated significantly by 121% the PAEC migration as compared to bFGF (10 ng/ml) alone (FIG. 6). Pretreatment of PAEC with ER antagonists ($10^{-7}$M) 5 min prior to 17βE addition prevented completely the chemotactic activity of 17βE ($10^{-8}$M) on PAEC (FIG. 6). We also investigated if the ER antagonists in absence of 17βE had an effect on PAEC bFGF chemotactic activity, and the ER antagonists did not alter the chemotactic activity of bFGF (10 ng/ml) on PAEC (data not shown).

Effects of 17βE on PAEC p42/44 and p38 MAPK Phosphorylation

Considering that 17βE can stimulate the proliferation and the migration of PAEC, we evaluated the effect of 17βE on phosphorylation of p42/44 and p38 MAPK of PAEC. Control PAEC (PBS-treated) showed a basal phosphorylation of p42/44 MAPK. Stimulation with 17βE ($10^{-8}$M) increased time-dependently at 5, 10, 15 and 30 minutes the phosphorylation of p42/44 MAPK by 1122%, 1074%, 1420% and 10 1835%, respectively (FIG. 7A). A pretreatment with Tam, 4-OHT or Ral ($10^{-7}$M) 5 min prior to the addition of 17βE decreased by 36%, 44% and 66% the phosphorylation of p42/44 MAPK induced by 5 min stimulation of 17βE ($10^{-8}$M) (FIG. 7B). As for p42/44 MAPK, a treatment of PAEC with 17βE ($10^{-8}$M) induced time-dependently the phosphorylation of p38 MAPK with a maximum stimulation at 30 minutes compared to unstimulated PAEC (PBS) (FIG. 8A). A pretreatment with ER antagonists ($10^{-7}$M) 5 min prior to the addition of 17βE inhibited by 84%, 81% and 98% the phosphorylation of p38 MAPK induced by a 30 minutes treatment with 17βE ($10^{-8}$ M) (FIG. 8B). A treatment with the ER antagonists in absence of 17βE did not affect the effect the basal phosphorylation of PAEC p42/44 and p38 MAPK (data not shown).

Discussion

We have previously demonstrated that a local delivery of 17βE upon a porcine coronary angioplasty reduces the degree of restenosis by up to 50% and improves the reendothelialization, eNOS expression and vascular healing[9]. In the present study, we observed that a treatment with 17βE stimulates the proliferation and the migration of PAEC following the phosphorylation of p42/44 and p38 MAPK, respectively. Interestingly, we showed that a treatment with 17βE reverses these events in PSMC.

Anti-mitogenic and Anti-chemotactic Effects of 17βE in PSMC

In response to vascular injury, the restenosis cascade is accompanied by VSMC migration and proliferation, extracellular matrix deposition and vascular remodelling. VSMC contribute to pathological formation of restenosis by migrating from media to the intima, proliferating, and depositing extracellular matrix proteins. Platelet-derived growth factor (PDGF), which is secreted from platelets and macrophages recruited at the early inflammatory lesion has been described to play an important role in restenosis. A previous study have shown that estrogen treatment can reduce post injury neointima formation in carotid arteries and aortas from animals[13]. In in vitro and in vivo experiments, other authors were able to demonstrate that estrogen can inhibit VSMC proliferation[3] and migration[4]. In the present study, a treatment with 17βE ($10^{-8}$ M) inhibited the proliferation and the migration of PSMC stimulated by PDGF-BB. We have demonstrated that PDGF-BB can activate the phosphorylation of p42/44 MAPK and p38 MAPK within 5 and 30 min respectively in PSMC. Treatment of these cells for 30 min with 17βE reduced the PDGF-BB induced phosphorylation of p42/44 and p38 MAPK by 100% and 85%, respectively. We showed that a pretreatment with ER antagonists inhibited the antimitogenic and anti-chemotactic effects of 17βE to prevent PDGF BB induced proliferation and migration. Also, these ER antagonists reversed the effect of 17βE to reduce the phosphorylation of p42/44 and p38 MAPK of PSMC stimulated by PDGF-BB suggesting that the effect of 17βE is mediated by the ER. A previous study have shown that selective ER modulators may have a potential positive effect on cardiovascular diseases[14]. In contrast, we have not observed any beneficial effect with these ER antagonists alone to prevent proliferation, migration or MAPK activity on PSMC treated with PDGF-BB.

17βE Promotes Reendothelialization by Increasing the Proliferation and the Migration of PAEC Hormone replacement therapy in postmenopausal women has been associated with improvement in some aspects of endothelial function[15]. Other studies have noted that administration of estrogen in healthy young men is associated with enhanced arterial endothelial function. We have shown that local delivery 15 of 17βE improve reendothelialization and eNOS expression after angioplasty[9]. In the present application, we propose that 17βE increases the proliferation and the migration of PAEC. Several evidence suggest that administration of estrogen increased rapidly the activation of eNOS[17]. In order to observe the non-genomic effect of 17βE in PAEC, we evaluated the MAPK activity of these cells following an administration of 17βE. Our results demonstrated that a treatment of PAEC with 17βE increased p42/44 and p38 MAPK phosphorylation within 5 and 30 min stimulation, respectively. Ranzandi et al. demonstrated that estrogen can preserve the actin cytoarchitecture during metabolic stress and induce the migration of endothelial cells leading to tube formation by stimulation of the p38 MAP K signal transduction pathway[8]. Our results suggest that the local effects of 17βE after vascular injury can promote endothelial regeneration and improve endothelial function through MAPK (p42/44 and p38 MAPK) pathways. Similar to PSMC studies, we evaluated the interaction of ER antagonists with 17βE. A pretreatment of PAEC with Tam, 4-OHT and Ral 5 reversed the phosphorylation of p42/44 and p38 MAPK mediated by 17βE. In addition, we did not observe any positive effect of treatment with ER antagonists alone on these MAPKs activity in PAEC.

An acute administration of 17-beta-estradiol therefore activates p42/44 and p38 MAPK to promote proliferation and migration of PAEC, and at the opposite, inhibits these events in PSMC. Classically, estrogen binds to its receptors and mediates effects on gene expression. Our results suggest that the beneficial effect of a treatment with 17βE on restenosis might be explained by a reduction of PSMC migration and proliferation combined to a positive endothelial cell migrating and proliferating activity.

Examples of in situ administration of 17 β-estradiol in a restenotic porcine model are given in co-pending applications CA 2,282,982 and CA 2,300,246. Examples of in situ administration of antisense molecules directed to other molecules than ER are given in CA 20 2,228,977. These three publications, the contents of which are herein incorporated by reference, provide guidelines as to the methods of administration, the pharmaceutical vehicles and approximate doses efficient in vivo to put into practice the present invention. Although the present invention has been described hereinabove by way of preferred embodiments thereof, it can be modified, without departing from the spirit and nature of the subject invention as defined in the appended claims.

Previous studies have demonstrated that disruption of ERα in mice reduce the cardioprotection effects of estrogen to prevent restenosis.[8] However, other investigators have indicated that ERβ, the major ER expressed on vasculature, may have a role on the beneficial effects of estrogen.[15] We have previously demonstrated that a local delivery of 17βE upon a porcine coronary angioplasty reduces the degree of restenosis by up to 50% and improves the reendothelialization, eNOS expression and vascular healing.[11,12] Recently, we have shown that an acute administration of 17βE increased PAEC proliferation and migration by up-regulating p42/44 and p38 MAPK, and prevented these same events on PSMC.[14] We have also suggested that these effects of 17βE were at least partially ER dependent. In the present study, we demonstrated that these effects of 17βE on PAEC were ERα-mediated. In contrast to PAEC, 17βE activities were mediated through ERβ on PSMC.

In conclusion, the properties of 17βE that promote the proliferation, the migration and the phosphorylation of p42/44 and p38 MAPK of PAEC are directly mediated to ERα. In contrast to this, 17βE inhibits p42/44 and p38 MAPK activation to stimulate proliferation and migration of PSMC, and these effects are ERβ-mediated. Our results suggest that the beneficial effects of estrogen may be induced differently on the two vascular cell types and provide new insights into our understanding of the mechanisms by which estrogen mediates its effects on vascular healing.

EXAMPLE 2

Antisense Oligonucleotide Therapy

To distinguish the role of ERα and ERβ on proliferation, migration and MAPK pathway of PAEC and PSMC, we treated these cells with antisense oligonucleotide sequences complementary to porcine ERα and ERβ mRNA (GeneBank accession numbers Z37167 and AF164957). A total of four different antisense oligonucleotide phosphothioate backbone sequences were used, two targeting porcine ERα mRNA (antisense 1, AS1-ERα: 5'-CTC GTT GGC TTG GAT CTG-3' (SEQ ID NO: 1); antisense 2: AS2-ERα: 5'-GAC GCT TTG GTG TGT AGG-3' (SEQ ID NO: 2)), and two targeting porcine ERβ mRNA (antisense 1, AS1-ERβ: 5'-GTA GGA GAC AGG AGA GTT-3' (SEQ ID NO: 3); antisense 2: AS2-ERβ: 5'-GCT AAA GGA GAG AGG TGT-3' (SEQ ID NO: 4)). Two scrambled phosphothioate sequences (scrambled ERα, SCR-ERα: 5'-TGT AGC TCG GTT CTG TCG-3' (SEQ ID NO: 13); scrambled ERβ, SCR-ERβ: 5'-GAG TGG ACG TGA AGA AGT-3' (SEQ ID NO: 14)) were also used as negative controls. These sequences were designed with no more than three consecutive guanosines and by minimizing their capacity to form hairpins and dimmers. All sequences were synthesized at the Armand Frappier Institute (Laval, Canada). After synthesis, the oligonucleotides were dried, resuspended in sterile water, and quantified by spectophotometry. The assurance that the antisense oligomer solutions were by-product-free was confirmed by denaturing polyacrylamide gel electrophoresis (20%; 7M urea), based on the known length of the oligonucleotide.

Materials and Methods

Western Blot Analysis of ERα and ERβ Protein Expression

The efficiency and specificity of our antisense sequences to block the targeted protein expression were evaluated by Western blot analysis. Culture medium of confluent PAEC and PSMC (100-mm tissue culture plate) were rinsed with Dulbecco's modified eagle medium (DMEM; Life Technologies Inc., Carlsbad, Calif.) and trypsinized (trypsine-EDTA; Life Technologies). Cells were resuspended in DMEM containing 5% of fetal bovine serum and antibiotics (penicillin and streptomycin, Sigma, St-Louis, Mo.), and a cell count was obtained with a Coulter counter Z1 (Coulter Electronics, Luton, UK). Cells were seeded at 1×10$^6$ cells/100-mm tissue culture plate (Becton-Dickinson, Rutherford, N.J.), stimulated for 24 h in DMEM, 5% FBS, and antibiotics with or without antisense oligomers ($10^{-7}$, $5 \times 10^{-7}$, $10^{-6}$ mol/L) and starved for 48 h in DMEM, 0.1% FBS, and antibiotics with or without antisense oligomers ($10^{-7}$, $5 \times 10^{-7}$, $10^{-6}$ mol/L daily) for G0 synchronization. LipofectAnime (5 μg/ml, Life Technology Inc) was used as a transfection reagent only on PSMC. The cells were then grown to confluence for 16 h in DMEM, 5% FBS, and antibiotics with or without antisense oligomers ($10^{-7}$, $5 \times 10^{-7}$, $10^{-6}$ mol/L) and starved for 7 h in DMEM, 0.1% FBS, and antibiotics with or without antisense oligomers ($10^{-7}$, $5 \times 10^{-7}$, $10^{-6}$ mol/L) to induce an up-regulation of the ER expression. Culture medium was removed, and cells were rinsed twice with ice-cold DMEM. Total proteins were prepared by the addition of 500 μl of lysis buffer containing phenylmethylsulfonyl fluoride 1 mM (Sigma), leupeptin 10 μg/ml (Sigma), aprotinin 30 μg/mi (Sigma), and NaVO$_3$ 1 mM (Sigma). Plates were incubated at 4° C. for 30 min and scraped, and the protein concentration was determined with a Bio-Rad protein kit (Bio-Rad, Hercules, Calif.). Same protein quantity for each cell type were dissolved in Laemmli's buffer, boiled for 5 min in reducing conditions, separated by a 10% gradient SDS-PAGE (Protean II kit; Bio-Rad), and transblotted onto a 0.45-μm polyvinylidene difluoride membranes (Millipore Corp., Bedford, Mass.). The membranes were blocked in 5% Blotto-TTBS (5% nonfat dry milk (Bio-Rad), 0.05% Tween 20, 0.15 M NaCl, 25 mM Tris-HCl, pH 7.5) for 1 h at room temperature with gentle agitation and incubated overnight in 0.5% Blotto-TTBS containing the desired antibody (rabbit polyclonal anti-ERα or anti-ERβ; 1:5000 dilution, Santa Cruz Biotechnology). Membranes were washed three times with TTBS, and incubated with a horseradish peroxidase goat anti-rabbit IgG antibody (1:10000 dilution,. Santa Cruz Biotechnology, Santa Cruz, Calif.) in 0.5% Blotto-TTBS for 30 min. Membranes were washed with TTBS, and horseradish peroxidase bound to secondary antibody was revealed by chemiluminescence (Renaissance kit, NEN Life Science Products, Boston, Mass.). Kaleidoscope molecular weight and SDS-polyacrylamide gel electrophoresis broad range marker proteins (Bio-Rad) were used as standards for SDS-polyacrylamide gel electrophoresis. Digital image densitometry (PDI Bioscience, Aurora, ON) was performed on x-ray films to determine relative percentages of ERα or ERβ protein expression. All western blot analysis was performed in triplicate and results of image densitometry are representative of these experiments.

Mitogenic Assay

Confluent PAEC and PSMC were rinsed with DMEM and trypsinized. Cells were resuspended in 10 mL of DMEM, 5% FBS, and antibiotics, and a cell count was obtained. PAEC and PSMC were initially seeded at 1×10$^4$ cells/well of 24-well tissue culture plates stimulated for 24 hours in DMEM, 5% FBS, and antibiotics with or without antisense oligomers ($10^{-6}$ mol/L), and starved for 48 hours in DMEM, 0.1% FBS, and antibiotics with or without antisense oligomers ($10^{-6}$ mol/L daily) for G0 synchronization. Initial cell number for growth was determined using a Coulter counter. The cells were stimulated for 72 hours in DMEM, 1% FBS, antibiotics with or without antisense oligomers ($10^{-6}$ mol/L daily) and with or without of 17βE (Sigma). After trypsinization, cell number was determined by using a Coulter counter.

Chemotactic Assay

Cell migration was evaluated using a modified Boyden 48-well microchamber kit (NeuroProbe, Cabin John, MD.). Near confluent PAEC and PSMC were rinsed with DMEM and trypsinized. Cells were resuspended in DMEM, 5% FBS, and antibiotics, and a cell count was obtained. PAEC and PSMC were seeded at 2.5×10$^5$ cells/well of 6-well tissue culture plates; stimulated for 24 hours in DMEM, 5% FBS, and antibiotics with or without antisense oligomers ($10^{-6}$ mol/L) and starved for 48 hours in DMEM, 0.1% FBS, and antibiotics with or without antisense oligomers ($10^{-6}$ mol/L daily) with or without 17βE ($10^{-8}$ mol/L). Cells were harvested by trypsinization and resuspended in DMEM, 1% FBS, and antibiotics at a concentration of 5×10$^5$ cells/mL. Fifty μL of this cell suspension with or without antisense oligomers ($10^{-6}$ mol/L) treated with or without 17βE ($10^{-8}$ mol/L) was added in the higher-chamber of the modified Boyden chamber apparatus, and the lower chamber was filled with DMEM, 1% FBS, antibiotics plus the desired concentration of agonist either 17βE ($10^{-8}$ mol/L) or platelet-derived growth factor-BB (PDGF-BB). The 2 sections of the system were separated by a porous polycarbonate filter (5-μm pores size), pretreated with a gelatine solution (1.5 mg/mL), and assembled. Five hours postincubation at 37° C., the non-migrated cells were scraped with a plastic policeman, and the migrated cells were stained using a Quick-Diff solution (Shandon Inc). The filter was then mounted on a glass slide, and migrated cells were counted using a microscope adapted to a video camera to obtain a computer-digitized image.

Western Blot Analysis of p38 and p42/44 MAPK Phosphorylation

Confluent PAEC and PSMC were preteated with or without antisense sequences as described above for Western Blot analysis. Cells were rinsed twice with ice-cold DMEM. PSMC and PAEC were stimulated with or without 17βE ($10^{-8}$ mol/L) as previously described (Geraldes P). Briefly, PSMC were incubated on ice in DMEM with or without 17βE ($10^{-8}$ mol/L) for 30 minutes, incubated at 37° C. for 30 minutes, then brought back on ice. Cells were then rinsed with cold DMEM, incubated on ice in DMEM, bovine serum albumin (1 mg/mL), PDGF-BB (10 ng/mL) for 30 minutes, incubated at 37° C. for 5 and 30 minutes, and then brought back on ice. PAEC were incubated on ice in DMEM with or without 17βE ($10^{-8}$ mol/L) for 30 minutes, then incubated at 37° C. for 5 and 30 minutes and brought back on ice. Total proteins were prepared-by the addition of 500 μL of lysis buffer, incubated at 4° C. for 30 minutes and scraped to collect the proteins. Same quantity of protein was separated by a 10% gradient SDS-PAGE (Protean II kit; Bio-Rad), and transblotted onto a 0.45-μm polyvinylidene difluoride membranes (Millipore Corp.). The membranes were blocked for 1 hour at room temperature with gentle agitation and incubated overnight at 4° C. in 0.5% Blotto-TTBS with the addition of an antiphospho p42/44 MAPK or an antiphospho p38 MAPK rabbit polyclonal antiserums (α-pp42/44; dilution of 1:10000, and α-pp38; dilution 1:5 000, New England BioLabs, Beverly, Mass.). Membranes were washed with TTBS, and incubated at room temperature with an anti-rabbit IgG antibody coupled to horseradish peroxidase (dilution 1:10 000–1:20 000, Santa Cruz Biotechnology) in 0.5% Blotto-TTBS for 30 minutes. Membranes were washed with TTBS, and horseradish peroxidase bound to secondary antibody was revealed by chemiluminescence (Renaissance kit, NEN Life Science Products). Digital image densitometry (PDI Bioscience) was performed on X-ray film to determine relative phosphorylation of p42/44 and p38 MAPK. All western blot analysis was performed in triplicate and results of image densitometry are representative of these experiments.

Statistical analysis—Data are mean±SEM. Statistical comparisons were performed using ANOVA followed by an unpaired Student t Test. A p value less than 0.05 was considered as significant.

Results

Modulation of ERα and ERβ Expression by Antisense Oligonucleotides

Figure 9:
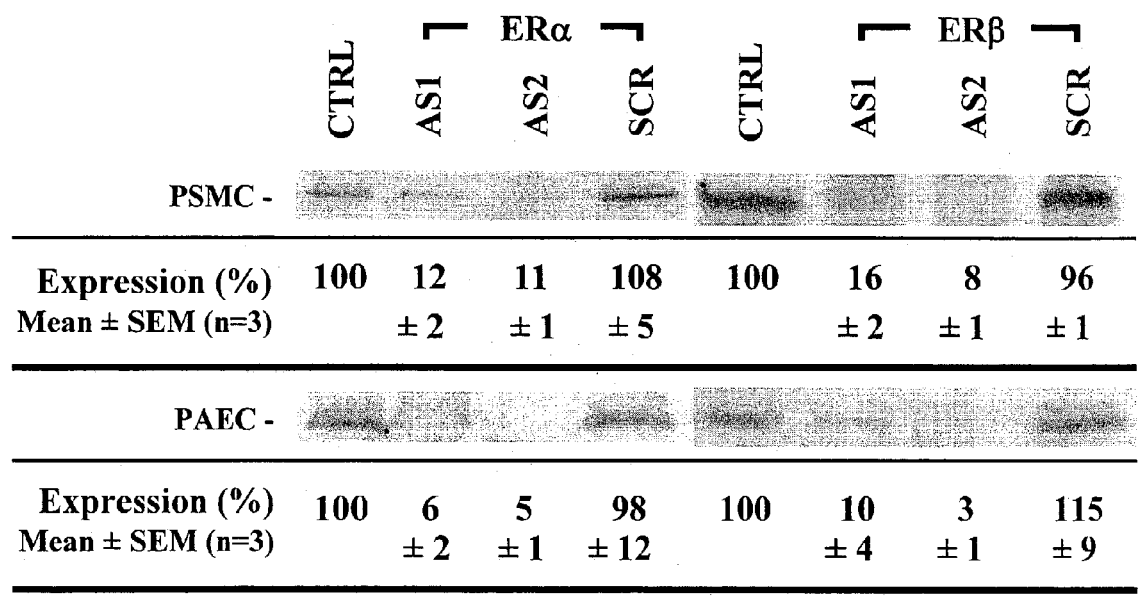
FIG. 9 Antisense regulation of ERα and ERβ expression on PSMC and PAEC. PSMC were seeded at $1 \times 10^6$ cells/100-mm culture plate and grown to confluence. Cells were treated either with antisense or scrambled sequences as described in methods. ERα and ERβ protein expression were detected by Western Blot analysis. Image densitometry results are given as relative expression (%) as compared with PBS-treated cells.

In order to evaluate the potency of antisense oligonucleotides to inhibit the targeted protein expression, PSMC and PAEC were treated with either the antisense or the scrambled oligonucleotide sequences. Total proteins were extracted, quantified by bioassay, and the expression of each receptor was determined by Western blot analysis. Digital image densitometry: was performed, and the results were expressed as relative expression pourcentage when compared with control PBS-treated cells. The basal protein expression of ERα (Ctrl) was inhibited when the PSMC and PAEC were pretreated with the two antisense oligomers directed against porcine ERα mRNA ($10^{-6}$ mol/L). The first antisense sequence (AS1-ERα) suppressed ERα protein expression by 88% on PSMC and 94% on PAEC, and the second antisense sequence (AS2-ERα) showed 89% inhibition effect on PSMC and 95% inhibition effect on PAEC (FIG. 9). Similar treatment with the two antisense sequences (AS1-ERβ and AS2-ERβ; $10^{-6}$ mol/L) complementary to ERβ mRNA inhibited PSMC basal ERβ protein expression by 84 and 92%, respectively (FIG. 9). The same series of experiments was performed with the two antisense sequence (AS1-ERβ and AS2-ERβ; $10^{-6}$ mol/L) down-regulated for the PAEC basal ERβ mRNA inhibited basal ERβ protein expression by 90 and 97%, respectively (FIG. 9). Two scrambled sequences (SCR-ERα and SCR-ERβ; $10^{-6}$ mol/L) had no suppressing effect on these ER expression as compared with the control PBS-treated cells (FIG. 9).

To ensure that the antisense oligomers designed to down-regulate the expression of ERα would not affect ERβ expression and vice versa, we performed a Western blot analysis to evaluate the specificity of our antisense oligomers. A pre-treatment with the antisense oligomers for the down-regulation of ERα ($10^{-6}$ mol/L) did not affect ERβ basal expression while our antisense oligomer sequences directed against ERβ mRNA ($10^{-6}$ mol/L) did not alter the basal expression of ERα0 on both PSMC and PAEC (data not shown).

Figure 10:
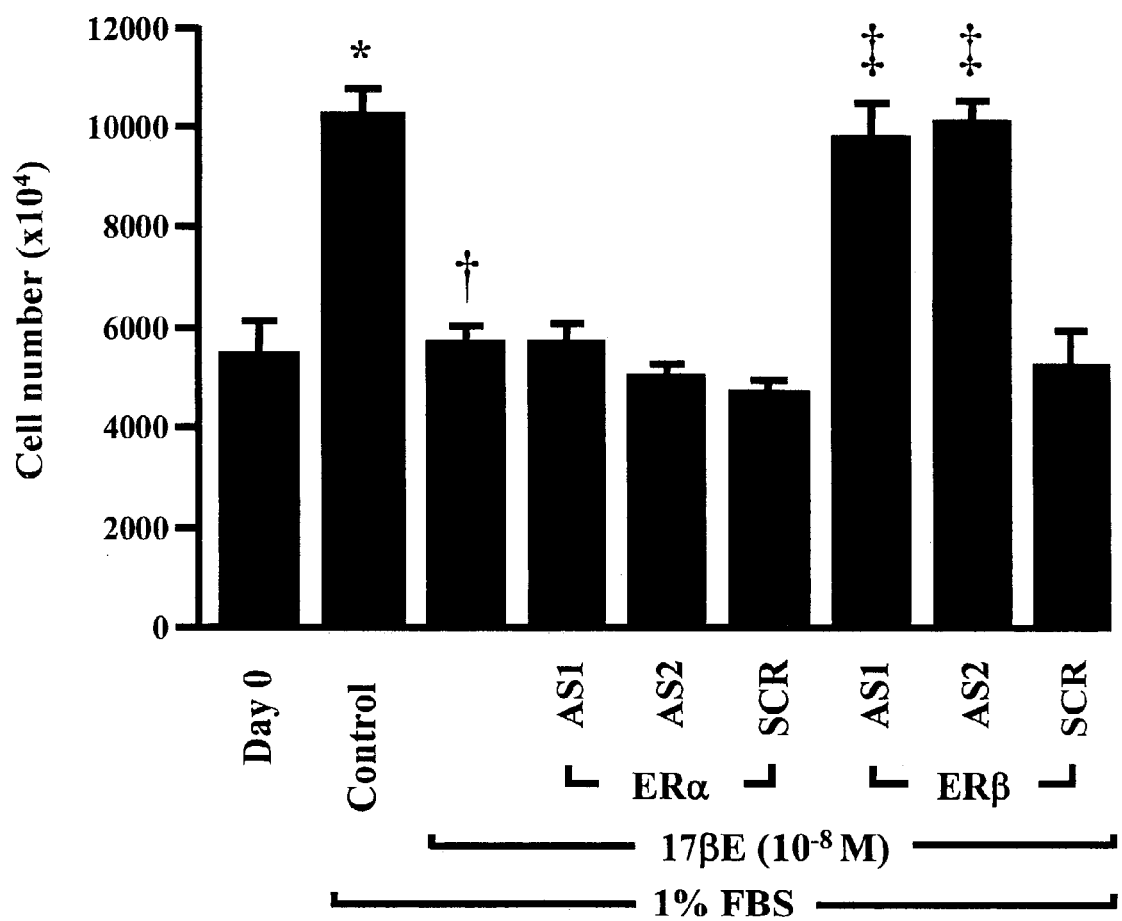
FIG. 10 Role of ERα and ERβ on 17βE effects on PSMC proliferation. PSMC were seeded at $1 \times 10^4$ cells/well and stimulated with or without antisense sequences as described in methods. The cells were then stimulated with or without. 17βE ($10^{-8}$ mol/L) and cell number was counted 72 h post treatment. The values are means of cell count obtained from 6 wells for each treatment. *, $P<0.05$ as compared to day 0; †, $P<0.05$ as compared to control; ‡, $P<0.05$ as compared to 17βE ($10^{-8}$ mol/L).

Effects of ERα and ERβ mRNA Antisense Oligonucleotides on 17βE Anti-Mitogenic Activity on PSMC Since the ER expressions were specifically blocked by antisense sequences described above, we investigated the effects of 17βE to distinguish the involvement of the two ER on PSMC proliferation. Stimulation of quiescent PSMC with DMEM 1% FBS increased significantly PSMC proliferation from 5432±680 cells/well to 10 216±546 cells/well (FIG. 10). Treatment with 17βE ($10^{-8}$ mol/L) prevented by 95% the PSMC proliferation mediated by FBS 1%. Then, by down-regulating the protein expression of ERα and ERβ by antisense gene therapy, we sought to evaluate the contribution of each ER to 17βE anti-mitogenic effects on PSMC. Pretreatment of PSMC with the two antisense sequences, complementary to porcine ERβ mRNA blocked significantly the effects of 17βE to inhibit PSMC proliferation ($P<0.05$), while the antisense sequences directed against ERα mRNA failed to prevent the anti-mitogenic effects of 17βE (FIG. 10). The scrambled oligonucleotide sequences did not affect 17βE-inhibited proliferation of PSMC.

Figure 11:
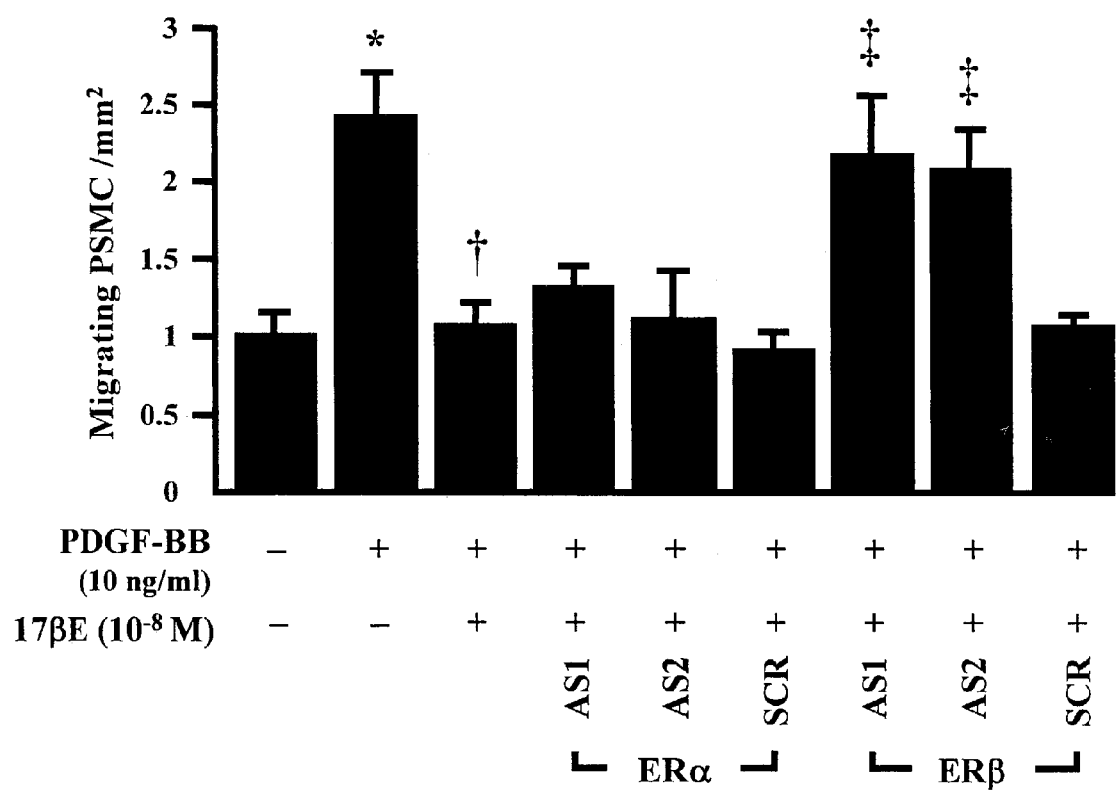
FIG. 11 Role of ERα and ERβ on 17βE effects on PSMC migration. PSMC were trypsinized and resuspended in DMEM; 2.5×10⁴ cell/were added in the higher chamber of the modified Boyden chamber apparatus, and the lower chamber was filled with DMEM 1% FBS, and antibiotics with or without PDGF-BB (10 ng/ml). Five hours post-incubation at 37° C., the migrated cells were stained and counted by using a microscope adapted to a digitized video camera. The values are means of migrating cells/mm² from 6 chambers for each treatment. *, P<0.05 as compared to day 0; †, P<0.05 as compared to control; ‡, P<0.05 as compared to 17βE ($10^{-8}$ mol/L).

Effects of Antisense Oligonucleotides Complementary to ERα and ERβ mRNA on 17βE Anti-Chemotactic Activity on PSMC Using a modified Boyden chamber assay, PDGF-BB (10 ng/mL) induced significantly the migration of PSMC by 199% as compared to DMEM 1%, 5 hours post-treatment (FIG. 11). A treatment with 17βE ($1^{-8}$ mol/L) inhibited completely the chemotactic effect of PDGF-BB (10 ng/mL) (FIG. 11). In order to evaluate the role of each ER subtype on 17βE anti-chemotactic effects on PSMC, PSMC were pretreated with the two antisense sequences down-regulated for the ERα mRNA ($10^{-6}$ mol/L) did alter the effects of 17βE to prevent PSMC migration induced by PDGF-BB.

However, a pretreatment with the two antisense oligomers directed against ERβ mRNA reversed significantly the anti-chemotactic effects of 17βE on PSMC (P<0.05). The scrambled sequences failed to influence 17βE activities to inhibit PSMC migration induced by PDGF-BB.

Figure 12:
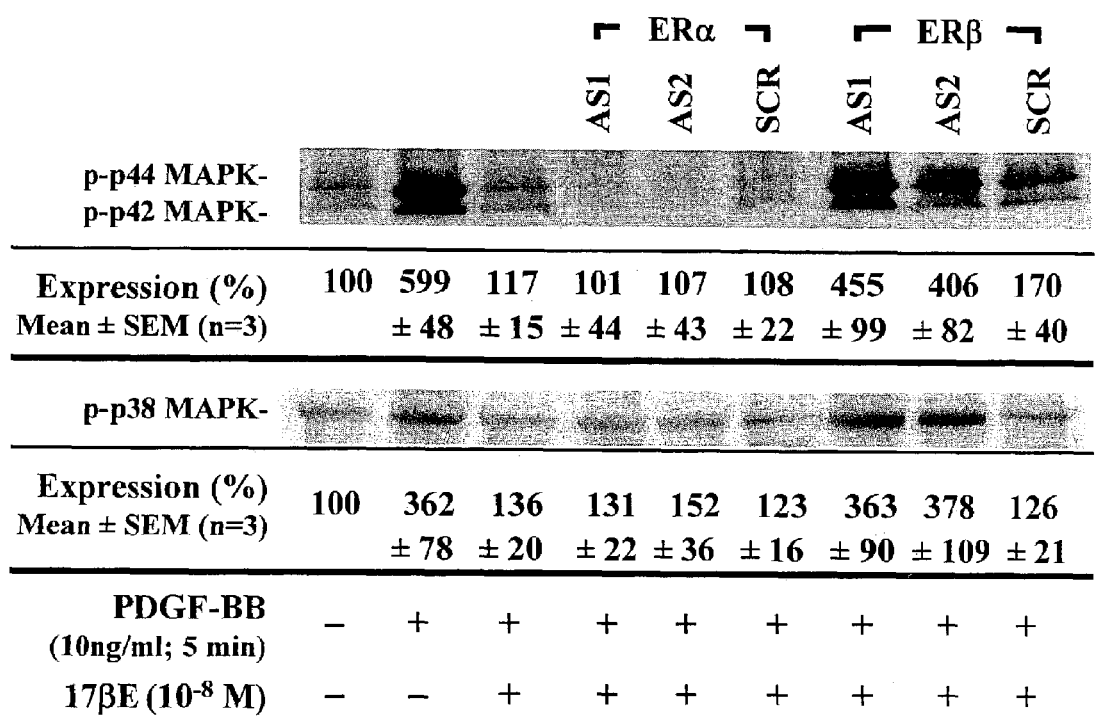
FIG. 12 Role of ERα and ERβ on 17βE effects on PSMC p42/44 and p38 MAPK activity. PSMC were seeded at 1×10⁶ cells/100-mm culture plate and grown to confluence. Cells were treated either with antisense or scrambled sequences as described in methods. Cells were then treated with or without 17βE ($10^{-8}$ mol/L) for 30 minutes and stimulated with PDGF-BB for 5 minutes for p42/44 MAPK and 30 minutes for p38 MAPK. Proteins were detected by Western Blot analysis. Image densitometry results are given as relative expression (%) as compared with PBS-treated cells.

Effects of 17βE on p42/44 and p38 MAPK Phosphorylation of PSMC Treated with ER mRNA Antisense Oligonucleotides Considering that 17βE can inhibit the proliferation, the migration and the phosphorylation of p42/44 and p38 MAPK of PSMC induced by PDGF-BB, we evaluated the specific role of each ER subtype that implicated in the anti-phosphorylation effects of 17βE. Stimulated PSMC with PDGF-BB increased p42/44 and p38 MAPK phosphorylation and these effects of PDGF-BB were reversed by a 30 minutes treatment with 17βE ($10^{-8}$ mol/L) (FIG. 12). Pretreatment of PSMC with antisense sequences complementary to ERα mRNA did not affect the effects of 17βE to prevent p42/44 and p38 MAPK induced by PDGF-BB. In contrast, pretreatment with antisense oligomers directed against ERβ mRNA blocked significantly the effects of 17βE to prevent PDGF-BB-induced p42/44 and p38 MAPK phosphorylation on PSMC (P<0.05). In the same series of experiments, scrambled antisense oligomers did not alter the activity of 17βE to inhibit the phosphorylation of these MAPKs.

Figure 13:
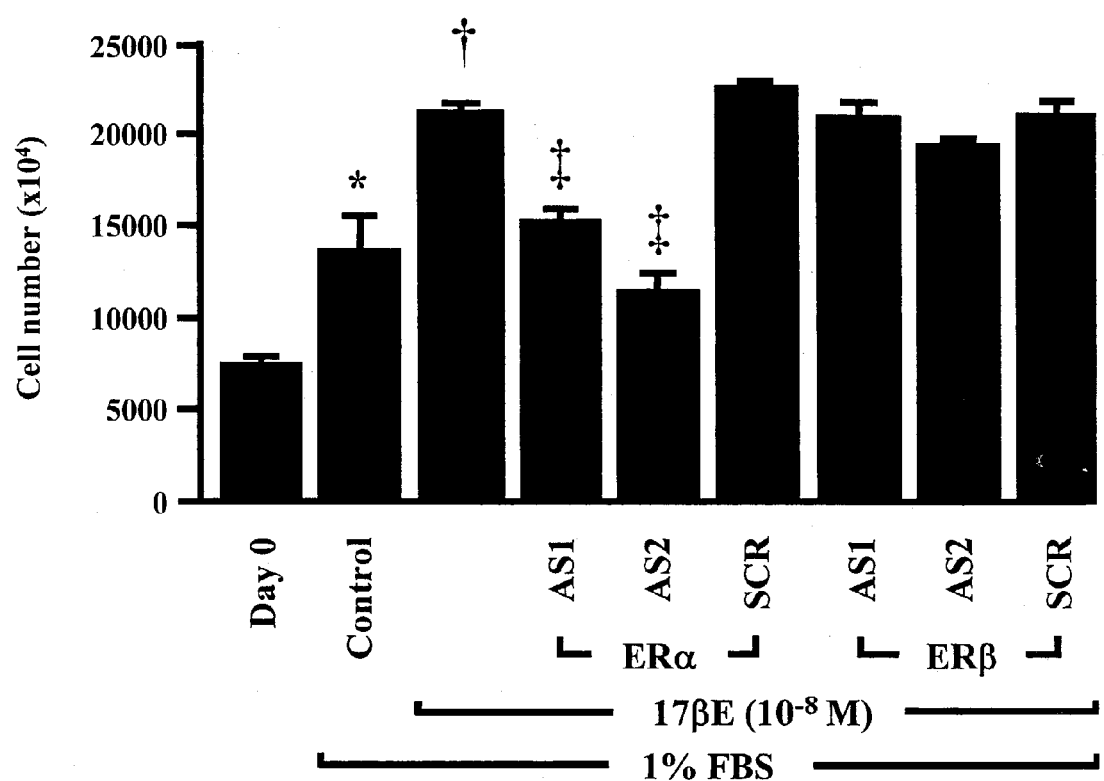
FIG. 13 Role of ERα and ERβ on 17βE effects on PAEC proliferation. PAEC were seeded at 1×10⁴ cells/well and stimulated with or without antisense sequences as described in methods. The cells were then stimulated with or without 17βE ($10^{-8}$ mol/L) and cell number was counted 72 h post treatment. The values are means of cell count obtained from 6 wells for each treatment. *, P<0.05 as compared to day 0; †, P<0.05 as compared to control; ‡, P<0.05 as compared to 17βE ($10^{-8}$ mol/L).

Effects of Antisense Oligonucleotide Sequences of ER Subtype mRNA on 17βE Mitogenic Activity on PAEC Nonstimulated PAEC showed a basal proliferation count of 7427±423 cells/well. Stimulated with DMEM 1% FBS raised proliferation cell count 13 566±1 931 cells/well. The addition of 17βE ($10^{-8}$ mol/L) induced the proliferation of PAEC by 123% over FBS 1% treatment (FIG. 13). To investigate how ER subtype influence the positive effects of 17βE on endothelial cells proliferation, quiescent PAEC were pretreated with antisense oligomer sequences of ERα mRNA which reduced significantly the mitogenic effects of 17βE (P<0.05). Pretreatment with antisense sequences complementary to ERβ mRNA failed to alter the proprieties of 17βE to induce PAEC proliferation. Again, PAEC treated with 17βE were not influenced by pretreatment with scrambled antisense oligomers.

Figure 14:
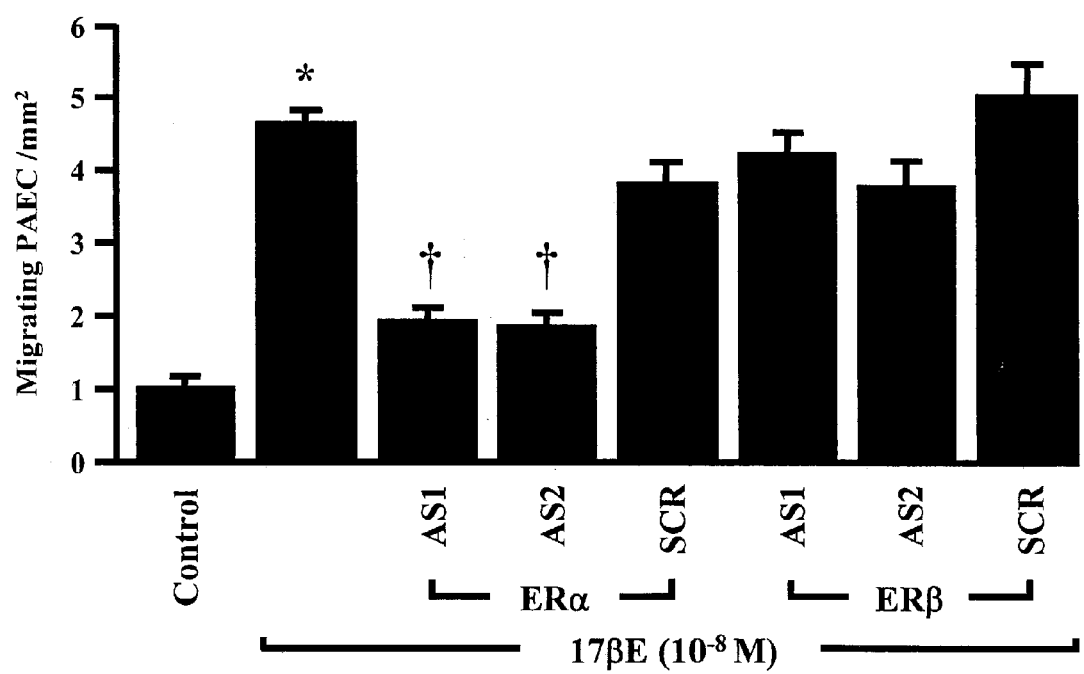
FIG. 14 Role of ERα and ERβ on 17βE effects on PAEC migration. PAEC were trypsinized and resuspended in DMEM; 2.5×10⁴ cell/were added in the higher chamber of the modified Boyden chamber apparatus, and the lower chamber was filled with DMEM 1% FBS, and antibiotics with or without PDGF-BB (10 ng/ml). Five hours postin-cubation at 37° C., the migrated cells were stained and counted by using a microscope adapted to a digitized video camera. The values are means of migrating cells/mm² from 6 chambers for each treatment. *, P<0.05 as compared to day 0; †, P<0.05 as compared to 17βE ($10^{-8}$ mol/L).

Effects on 17βE Chemotactic Activity of ER Subtype mRNA Antisense Oligonucleotides on PAEC A treatment with 17βE ($10^{-8}$ mol/L) induced of 4.63-fold the migration of PAEC in 5 hours as compared to DMEM 1% (P<0.05). PAEC were treated with ER mRNA antisense sequences ($10^{-6}$ mol/L), but only antisense oligomers down-regulated for the ERα mRNA prevented completely the chemotactic activity of 17βE ($10^{-8}$ mol/L) on PAEC (P<0.05) (FIG. 14). We did not observe any inhibitory effects in absence of ERβ protein expression or with scrambled antisense sequences.

Figure 15:
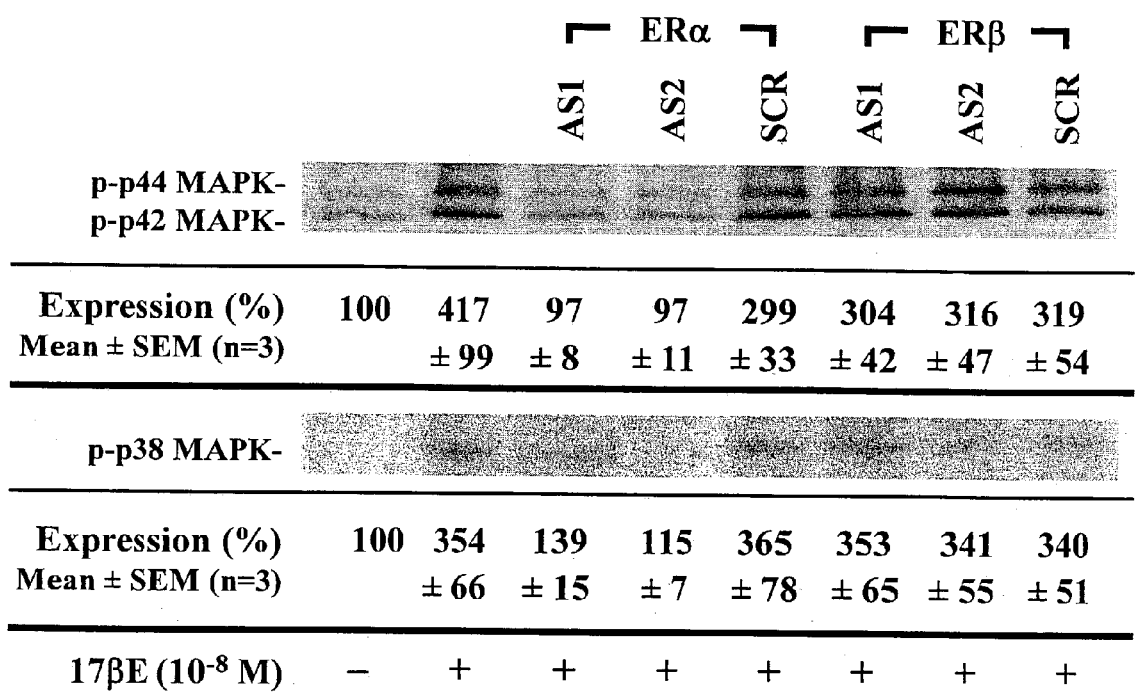
FIG. 15 Role of ERα and ERβ on 17βE effects on PAEC p42/44 and p38 MAPK activity. PAEC were seeded at 1×10⁶ cells/100-mm culture plate and grown to confluence. Cells were treated either with antisense or scrambled sequences as described in methods. Cells were then treated with or without 17βE ($10^{-8}$ mol/L) for 5 minutes for p42/44 MAPK and for 30 minutes for p38 MAPK. Proteins were detected by Western Blot analysis. Image densitometry results are given as relative expression (%) as compared with PBS-treated cells.

Effects of ERα and ERβ mRNA Antisense Oligonucleotides on 17βE-Induced p42/44 and p38 MAPK Phosphorylation on PAEC We have previously demonstrated that 17βE induced an intense phosphorylation of p42/44 and p38 MAPK on PAEC. In other to determine the role of ERα and ERβ on these intracellular mechanisms, PAEC were treated with antisense oligonucleotide sequences (FIG. 15). PBS-treated PAEC showed a basal phosphorylation of p42/44 and p38 MAPK. Stimulation with 17βE ($10^{-8}$ mol/L) for 5 and 30-minutes increased the phosphorylation of p42/44 MAPK by 329%, and p38 MAPK phosphorylation by 254%, respectively. A pretreatment with antisense sequence complementary to ERα mRNA prevented phosphorylation of p42/44 and p38 MAPK on these cells. In contrast, a pretreatment with antisense oligomer sequences failed to alter protein expression ERβ did not alter 17βE activity to induce the phosphorylation of p42/44 and p38 MAPK. Indeed, scrambled antisense sequences did not influence the p42/44 and p38 MAPK phosphorylation mediated by 17βE treatment.

Discussion

Inhibition of ERα and ERβ mRNA Expression using Antisense Oligomers

Several studies have used different therapies to suppress ER expression, like adenoviral delivery of a dominant negative ER to ER positive breast cancer cell.[36] In our study, we used antisense gene therapy to eliminate specifically each ER protein expression. This approach allowed evaluating separately the role of each ER on intracellular pathways in native endothelial and smooth muscle cells. The two antisense oligonucleotide sequences for the ERα mRNA and the two others for the ERβ mRNA did not contain more than three consecutive guanosines to avoid a possible interference with serum proteins.[37] Inamdar and co-workers have shown that brain ERα protein levels in rat were decreased by 65% at 6 h and 35% at 24 h after antisense oligonucleotide therapy.[33] As shown by Western blot analysis, we demonstrated that treatment of PSMC with the AS2 ($10^{-6}$ mol/L) for 4 days period decreased ERα and ERβ expression by 89% and 92%, respectively (FIG. 9). In a same series of experiments, AS2 ($10^{-6}$ mol/L) were able to decrease ERα and ERβ expression on PAEC by 95% and 97%, respectively (FIG. 9). Our system also provided the possibility to evaluate if the heterodimerization of ER are required to observe the biological effects of 17βE.

ERα and ERβ Activity on Anti-mitogenic and Anti-chemotactic Effects of 17βE in PSMC Usually activated by growth factors and cytokines, SMC proliferation and migration remain a major problem for in-stent restenosis. Many studies have indicated that estrogen prevent restenosis formation by inhibiting SMC proliferation and migration after balloon injury. We have previously demonstrated that 17βE decreased p42/44 and p38 MAPK phosphorylation, implicated in cell proliferation and migration, induced by PDGF-BB. In the present study, a treatment with 17βE ($10^{-8}$ mol/L) inhibited the proliferation and the migration of PSMC stimulated by PDGF-BB. When PSMC were pretreated with antisense sequences directed against ERβ protein expression, the effects of 17βE to prevent the proliferation and the migration of PSMC were reversed. Our results support other studies which have shown that loss of ERβ accompanies proliferative disease and that knock-out of ERβ leads to hyperproliferation in the mouse uterus.[38] It is also well established that estrogen can interact with various intracellular signal pathway such as kinases.[38] We have recently demonstrated that 17βE reduce the phosphorylation of p42/44 MAPK and p38 MAPK in PSMC induced by PDGF-BB. To better understand which ER regulates these nongenomic effects of estrogen, we have shown that pretreatment with antisense oligomer sequences down-regulated for the ERβ mRNA abrogate the effects of 17βE to inhibit the phosphorylation of p42/44 and p38 MAPK mediated by PDGF-BB. Several studies have observed that ERβ is upregulated in rat carotid artery after injury[40] and this isoform is responsible for attenuation of vasoconstriction in animal induced by estrogen.[30] In contrast to ERβ, the absence of ERα protein expression did not influence the properties of 17βE to influence p42/44 and p38 MAPK phosphorylation of PSMC.

ERα is Required to 17βE-induced Reendothelialization of PAEC

Various conditions such as hypercholesterolemia, hypertention, inflammation, and estrogen deficiency have been associated with endothelium dysfunction.[24] The vessel wall impairment may contribute to the development of atherosclerosis and coronary vascular disease. Several animal and in vitro studies have shown that the properties of estrogen to improve endothelial function have been attributed to the acute and the long term effects of estrogen in multiples mechanisms. We have also demonstrated that local delivery of 17βE improves vascular healing and reendothelialization by promoting endothelial cell proliferation and migration. In the present study, we have shown that the beneficial effects on endothelial regeneration of 17βE were mediated by ERα. Our results indicated that a treatment with antisense sequences complementary to ERα mRNA inhibit the mitogenic and the chemotactic effects of 17βE on PAEC. Brouchet and coworkers have noted that only ERα is required for estrogen-accelerated reendothelialization in perivascular injury model.[41] Numerous experiments have demonstrated that rapid actions of estrogen on endothelial cells were associated with NO production and e-NOS expression. Several pieces of evidence suggested that estrogen activates eNOS by ERα-induced intracellular signalling pathway.[42] Estrogen can also interact with MAPK pathway[43] and we have previously demonstrated that 17βE induced p42/44 and p38 MAPK activation on endothelial cells. In order to determine the role of each ER in these mechanisms, PAEC were pretreated with antisense oligomer sequences. We have shown that ERα expression inhibition is associated to a reduction of p42/44 and p38 MAPK phosphorylation induced by 17βE. These results are consistent with those of previous work who were able to indicate a strength relationship with ERα and MAPK activity[44], and other study which have noted that ERα, and not ERβ, meditates the long term effects of estrogen NO production in intact endothelial cells.[45]

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

1. Cignarella A, Paoletti R, Puglisi L. Direct effects of estrogen on the vessel wall. *Med Res Rev.* 2001;21: 171–84.
2. Song J, Wan Y, Rolfe B E et al. Effect of estrogen on 5 vascular smooth muscle cells is dependent upon cellular phenotype. *Atherosclerosis.* 1998; 140:97–104.
3. Lavigne M C, Ramwell P W, Clarke R. Inhibition of estrogen receptor function promotes porcine coronary artery smooth muscle cell proliferation. *Steroids.* 1999; 64:472–80.
4. Akishita M, Ouchi Y, Miyoshi H et al. Estrogen inhibits cuff-induced intimal thickening of rat femoral artery: effects on migration and proliferation of vascular smooth muscle cells. *Atherosclerosis.* 1997;130:1–10.
5. Lantin-Hermoso R L, Rosenfeld C R, Yuhanna I S et al. 15 Estrogen acutely stimulates nitric oxide synthase activity in fetal pulmonary artery endothelium. Am J Physiol. 1997;2731119–26.
6. Herrington D. Role of estrogens, selective estrogen receptor modulators and phytoestrogens in cardiovascular protection. Can *J Cardiol.* 2000;16 Suppl E:5E–9E.
7. Cenci S, Weitzmann M N, Roggia C et al. Estrogen deficiency induces bone loss by enhancing T-cell production of TNF-alpha. *J Clin Invest.* 2000; 106:1229–37.
8. Silbiger S, Lei J, Ziyadeh F N et al. Estradiol reverses TGF-beta1-stimulated type IV collagen gene transcription in murine mesangial cells.: Am J Physiol. 1998;274: FI113–8.
9. Chandrasekar B, Tanguay J F. Local delivery of 175 beta-estradiol decreases neointimal hyperplasia after coronary angioplasty in a porcine model. J Am Coll Cardiol. 2000;36:1972–8.
10. Mendelsohn M E, Karas R H. The protective effects of estrogen on the cardiovascular system. N Engl J Med. 1999;340:180111.
11. Hayashi K, Takahashi M, Kimura K et al. Changes in the balance of phosphoinositide 3-kinase/protein kinase B (Akt) and the mitogen-activated protein kinases (ERK/p38MAPK) determine a phenotype of visceral and vascular smooth muscle cells. J Cell Biol. 1999;145:727–40.
12. Simoncini T,. Genazzani A R. Direct vascular effects of estrogens and selective estrogen receptor modulators. Curr Opin Obstet Gynecol. 2000;12:181–7.
13. Finking G, Krauss N, Romer S et al. 17-beta-estradiol, gender independently, reduces atheroma development but not 20 neointimal proliferation after balloon injury in the rabbit aorta. Atherosclerosis. 2001; 154:39–49.
14. Clarke S C, Schofield P M, Grace A A et al. Tamoxifen effects on endothelial function and cardiovascular risk factors in men wit advanced atherosclerosis. Circulation. 2001:103:1497–502.
15. Van Baal W M, Kenemans P, Emeis J J et al. Longterm effects of combined hormone replacement therapy on markers of endothelial function and inflammatory activity in healthy postmenopausal 5 women. Fertil Steril. 1999; 71 :663–70.
16. Sader M A, McCredie R J, Griffiths K A et al. Oestradiol improves arterial endothelial function in healthy men receiving testosterone. Clin Endocrinol (Oxf). 2001;54: 175–81.
17. Shaul P W. Novel role of estrogen receptors in 10 vascular endothelium. Semin Perinatol. 2000;24:70–4.
18. Razandi M, Pedram A, Levin E R. Estrogen signals to the preservation of endothelial cell form and function. J Biol Chem. 2000;275:38540–6.
19. Giguere V, Tremblay A, Tremblay G B. Estrogen 15 receptor beta: re-evaluation of estrogen and antiestrogen signaling. Steroids. 1998;63:335–9.
20. Brzozowski A M, Pike A C, Dauter Z, Hubbard R E, Bonn T, Engstrom O, Ohman L, Greene G L, Gustafsson J A, Carlquist M. Molecular basis of agonism and antagonism in the oestrogen receptor. 20 Nature. 1997;389: 753–8.
21. Evans M J, Harris H A, Miller C P, Karathanasis S K, Adelman S J. Estrogen receptors alpha and beta have similar activities in multiple endothelial cell pathways. *Endocrinology.* 2002;143:3785–95.
22. Grodstein F, Manson J E, Stampfer M J. Postmenopausal hormone use and secondary prevention of coronary events in the nurses' health study a prospective, observational study. *Ann Intern Med.* 2001;135:1–8.

23. Nelson H D, Humphrey L L, Nygren P, Teutsch S M, Allan J D. Postmenopausal hormone replacement therapy: scientific review. *Jama.* 2002;288:872–81.
24. Koh K K. Effects of estrogen on the vascular wall: vasomotor function and inflammation. *Cardiovasc Res.* 2002;55:714–26.
25. Keshamouni V G, Mattingly R R, Reddy K B. Mechanism of 17-beta-estradiol-induced Erk1/2 activation in breast cancer cells. A role for HER2 AND PKC-delta. *J Biol Chem.* 2002;277:22558–65.
26. Mendelsohn M E. Mechanisms of estrogen action in the cardiovascular system. *J Steroid Biochem Mol Biol.* 2000; 74:337–43.
27. Luconi M, Forti G, Baldi E. Genomic and nongenomic effects of estrogens: molecular mechanisms of action and clinical implications for male reproduction. *J Steroid Biochem Mol Biol.* 2002;80:369–81.
28. Pare G, Krust A, Karas R H, Dupont S, Aronovitz M, Chambon P, Mendelsohn M E. Estrogen receptor-alpha mediates the protective effects of estrogen against vascular injury. *Circ Res.* 2002;90:1087-92.
29. Simoncini T, Fornari L, Mannella P, Varone G, Caruso A, Liao J K, Genazzani A R. Novel non-transcriptional mechanisms for estrogen receptor signaling in the cardiovascular system. Interaction of estrogen receptor alpha with phosphatidylinositol 3-OH kinase. *Steroids.* 2002; 67:935–9.
30. Zhu Y, Bian Z, Lu P, Karas R H, Bao L, Cox D, Hodgin J, Shaul P W, Thoren P, Smithies O, Gustafsson J A, Mendelsohn M E. Abnormal vascular function and hypertension in mice deficient in estrogen receptor beta. *Science.* 2002;295:505–8.
31. Chandrasekar B, Tanguay J F. Local delivery of 17-beta-estradiol decreases neointimal hyperplasia after coronary angioplasty in a porcine model. *J Am Coll Cardiol.* 2000;36:1972–8.
32. Chandrasekar B, Nattel S, Tanguay J F. Coronary artery endothelial protection after local delivery of 17-beta-estradiol during balloon angioplasty in a porcine model: a potential new pharmacologic approach to improve endothelial function. *J Am Coll Cardiol.* 2001;38:1570-6.
33. Inamdar S R, Eyster K M, Schlenker E H. Estrogen receptor-alpha antisense decreases brain estrogen receptor levels and affects ventilation in male and female rats. *J Appl Physiol.* 2001;91:1886–92.
34. Geraldes P, Sirois M G, Bernatchez P N, Tanguay J F. Estrogen regulation of endothelial and smooth muscle cell migration and proliferation: role of p38 and p42/44 mitogen-activated protein kinase. *Arterioscler Thromb Vasc Biol.* 2002;22:1585–90.
35. Arnal J F, Bayard F. Alteration in endothelial estrogen receptor expression: a potential key of vasculoprotection by estrogens? *Circ Res.* 2002;91:759–60.
36. Lazennec G, Alcorn J L, Katzenellenbogen B S. Adenovirus-mediated delivery of a dominant negative estrogen receptor gene abrogates estrogen-stimulated gene expression and breast cancer cell proliferation. *Mol Endocrinol.* 1999; 13:969–80.
37. Stein C A. Does antisense exist? *Nat Med.* 1995; 1:1119–21.
38. Liu M M, Albanese C, Anderson C M, Hilty K, Webb P, Uht R M, Price R H, Jr., Pestell R G, Kushner P J. Opposing action of estrogen receptors alpha and beta on cyclin D1 gene expression. *J Biol Chem.* 2002;277: 24353–60.
39. Levin E R. Cellular functions of plasma membrane estrogen receptors. *Steroids.* 2002;67:471–5.
40. Makela S, Savolainen H, Aavik E, Myllarniemi M, Strauss L, Taskinen E, Gustafsson J A, Hayry P. Differentiation between vasculoprotective and uterotrophic effects of ligands with different binding affinities to estrogen receptors alpha and beta. *Proc Natl Acad Sci U S A.* 1999;96:7077–82.
41. Brouchet L, Krust A, Dupont S, Chambon P, Bayard F, Arnal J F. Estradiol accelerates reendothelialization in mouse carotid artery through estrogen receptor-alpha but not estrogen receptor-beta. *Circulation.* 2001;103:423–8.
42. Haynes M P, Sinha D, Russell K S, Collinge M, Fulton D, Morales-Ruiz M, Sessa W C, Bender J R. Membrane estrogen receptor engagement activates endothelial nitric oxide synthase via the PI3-kinase-Akt pathway in human endothelial cells. *Circ Res.* 2000;87:677–82.
43. Song R X, McPherson R A, Adam L, Bao Y, Shupnik M, Kumar R, Santen R J. Linkage of rapid estrogen action to MAPK activation by ERalpha-Shc association and Shc pathway activation. *Mol Endocrinol.* 2002;16:116–27.
44. Lu Q, Ebling H, Mittler J, Baur W E, Karas R H. MAP kinase mediates growth factor-induced nuclear translocation of estrogen receptor alpha. *FEBS Lett.* 2002;516:1–8.
45. Darblade B, Pendaries C, Krust A, Dupont S, Fouque M J, Rami J, Chambon P, Bayard F, Arnal J F. Estradiol alters nitric oxide production in the mouse aorta through the alpha-, but not beta-, estrogen receptor. *Circ Res.* 2002; 90:413–9.

What is claimed is:

1. An antisense oligonucleotide complementary to a gene encoding a mammalian vascular estrogen receptor (ER) beta, wherein said antisense oligonucleotide is about 18 to about 25 nucleotides in length and is complementary to said gene, and wherein said antisense oligonucleotide comprises the nucleotide sequence of SEQ ID NO: 10.

2. The antisense oligonucleotide according to claim 1, wherein said mammalian vascular estrogen receptor (ER) is human ER-beta.

3. A composition comprising a pharmaceutically acceptable carrier and an antisense oligonucleotide complementary to a gene encoding a mammalian vascular estrogen receptor (ER) beta, wherein said antisense oligonucleotide is about 18 to 20 nucleotides in length and is complementary to said gene, and wherein said antisense oligonucleotide comprises the nucleotide sequence of SEQ ID NO: 10.

4. An antisense oligonucleotide as defined in claim 1, wherein said oligonucleotide has no more than three consecutive guanosines, has an incapacity to form hairpin structures and has a minimal capacity to form homodimers.

5. A composition comprising a pharmaceutically acceptable carrier and an antisense oligonucleotide as defined in claim 1.

6. The antisense oligonucleotide of claim 1 that is contained within an expression vector.

7. The antisense oligonucleotide of claim 1 that is modified in a manner selected from the group consisting of a modified backbone, a non-natural internucleoside linkage, a substituted sugar moiety, a sugar mimetic, a nucleobase modification, a nucleobase substitution, a chemically linked moiety, and a chemically linked conjugate.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Porcine AS1-ER-alpha

<400> SEQUENCE: 1
ctcgttggct tggatctg                                                    18

<210> SEQ ID NO 2
<211> LENGTH: 18
<212> TYPE: DNA
<213> ORGANISM: Porcine AS2-ER-alpha

```
<400> SEQUENCE: 2
gacgctttgg tgtgtagg                                                 18

<210> SEQ ID NO 3
<211> LENGTH: 18
<212> TYPE: DNA
<213> ORGANISM: Porcine AS1-ER-beta

<400> SEQUENCE: 3
gtaggagaca ggagagtt                                                 18

<210> SEQ ID NO 4
<211> LENGTH: 18
<212> TYPE: DNA
<213> ORGANISM: Porcine AS2-ER-beta

<400> SEQUENCE: 4
gctaaaggag agaggtgt                                                 18

<210> SEQ ID NO 5
<211> LENGTH: 18
<212> TYPE: DNA
<213> ORGANISM: Human AS1-ER-alpha

<400> SEQUENCE: 5
aacgccgcag cctcagac                                                 18

<210> SEQ ID NO 6
<211> LENGTH: 18
<212> TYPE: DNA
<213> ORGANISM: Human AS2-ER-alpha

<400> SEQUENCE: 6
ccgaacgccg cagcctca                                                 18

<210> SEQ ID NO 7
<211> LENGTH: 18
<212> TYPE: DNA
<213> ORGANISM: Human AS3-ER-alpha

<400> SEQUENCE: 7
gatgctttgg tgtggagg                                                 18

<210> SEQ ID NO 8
<211> LENGTH: 18
<212> TYPE: DNA
<213> ORGANISM: Human AS4-ER-alpha

<400> SEQUENCE: 8
cgttgaactc gtaggcgg                                                 18

<210> SEQ ID NO 9
<211> LENGTH: 18
<212> TYPE: DNA
<213> ORGANISM: Human AS1-ER-beta

<400> SEQUENCE: 9
agatggtgag tttttat                                                  18

<210> SEQ ID NO 10
<211> LENGTH: 18
<212> TYPE: DNA
```

```
<213> ORGANISM: Human AS2-ER-beta

<400> SEQUENCE: 10
tgtaggagga aggagaat                                              18

<210> SEQ ID NO 11
<211> LENGTH: 18
<212> TYPE: DNA
<213> ORGANISM: Human AS3-ER-beta

<400> SEQUENCE: 11
gttgtaggag gaaggaga                                              18

<210> SEQ ID NO 12
<211> LENGTH: 18
<212> TYPE: DNA
<213> ORGANISM: Human AS4-ER-beta

<400> SEQUENCE: 12
taggaggaag gtatgtat                                              18

<210> SEQ ID NO 13
<211> LENGTH: 18
<212> TYPE: DNA
<213> ORGANISM: Scrambled phosphothioate ER-alpha

<400> SEQUENCE: 13
tgtagctcgg ttctgtcg                                              18

<210> SEQ ID NO 14
<211> LENGTH: 18
<212> TYPE: DNA
<213> ORGANISM: Scambled phosphothioate ER-beta

<400> SEQUENCE: 14
gagtggacgt gaagaagt                                              18
```